(12) United States Patent
Cargol

(10) Patent No.: US 10,542,906 B2
(45) Date of Patent: Jan. 28, 2020

(54) TOMOGRAPHIC SYSTEMS AND METHODS FOR DETERMINING CHARACTERISTICS OF INHOMOGENOUS SPECIMENS USING GUIDED ELECTROMAGNETIC FIELDS

(71) Applicant: Spectrohm, Inc., Tysons Corner, VA (US)

(72) Inventor: Timothy L. Cargol, McLean, VA (US)

(73) Assignee: Spectrohm, Inc., Tysons Corner, VA (US)

(*) Notice: Subject to any disclaimer, the term of this patent is extended or adjusted under 35 U.S.C. 154(b) by 0 days.

(21) Appl. No.: 16/378,425

(22) Filed: Apr. 8, 2019

(65) Prior Publication Data

US 2019/0328267 A1    Oct. 31, 2019

Related U.S. Application Data

(60) Provisional application No. 62/662,594, filed on Apr. 25, 2018, provisional application No. 62/781,846, filed on Dec. 19, 2018.

(51) Int. Cl.
*A61B 5/05* (2006.01)
*A61B 5/00* (2006.01)
*A61B 5/053* (2006.01)

(52) U.S. Cl.
CPC .......... *A61B 5/0536* (2013.01); *A61B 5/0002* (2013.01); *A61B 2562/0223* (2013.01)

(58) Field of Classification Search
None
See application file for complete search history.

(56) References Cited

U.S. PATENT DOCUMENTS 4,135,131 A   1/1979  Larsen et al.
4,240,445 A  12/1980  Iskander et al.
(Continued)

FOREIGN PATENT DOCUMENTS

WO    WO2019209556 A1    10/2019

OTHER PUBLICATIONS

Taylor, John et al., "Open-Wire Transmission Lines Applied to the Measurement of the Macroscopic Electrical Properties of a Forest Region", Stanford Research Institute, Oct. 1971, 131 pages.
(Continued)

*Primary Examiner* — Patricia J Park
(74) *Attorney, Agent, or Firm* — Carr & Ferrell LLP

(57) ABSTRACT

A system for determining characteristics of a specific region within an inhomogeneous dielectric specimen by guiding propagation of electric fields through the inhomogeneous dielectric specimen is provided herein. Various embodiments include at least one source of electromagnetic energy for generating electromagnetic waveforms, the electromagnetic waveforms comprising electric fields propagating along a prescribed path that defines a series of spatial regions through which the electric fields propagate. In some embodiments the prescribed path includes electric field modulating elements that determine a rate of electric field propagation along the prescribed path. Some embodiments include a plurality of conductors for guiding the electric field propagation through an inhomogeneous dielectric specimen in the prescribed path, the electric fields spanning between two or more of the plurality of conductors as the electric fields propagate along the prescribed path. In some embodiments the plurality of conductors are external to the inhomogeneous dielectric specimen.

19 Claims, 22 Drawing Sheets

(56) References Cited

U.S. PATENT DOCUMENTS

| | | | |
|---|---|---|---|
| 4,493,039 A * | 1/1985 | Gregory | G01N 27/82 |
| | | | 324/228 |
| 5,119,034 A | 6/1992 | Ishikawa et al. | |
| 5,807,251 A | 9/1998 | Wang et al. | |
| 7,164,105 B2 | 1/2007 | Godshalk et al. | |
| 7,205,782 B2 | 4/2007 | Hawkins et al. | |
| 7,660,452 B2 | 2/2010 | Zwirn et al. | |
| 7,664,303 B2 | 2/2010 | Zwirn et al. | |
| 8,010,187 B2 | 8/2011 | Freed et al. | |
| 8,391,968 B2 | 3/2013 | Ginor et al. | |
| 8,762,084 B2 | 6/2014 | Gao et al. | |
| 8,933,837 B2 | 1/2015 | Okhmatovski | |
| 9,042,957 B2 | 5/2015 | Li et al. | |
| 9,074,922 B2 | 7/2015 | Dayal et al. | |
| 9,110,115 B2 | 8/2015 | Marashdeh et al. | |
| 2004/0130491 A1 * | 7/2004 | Hayes | H01P 1/2005 |
| | | | 343/701 |
| 2004/0246079 A1 | 12/2004 | Ehata | |
| 2005/0093555 A1 | 5/2005 | Ehata | |

OTHER PUBLICATIONS

Stuchly, Maria A., "Coaxial Line Reflection Methods for Measuring Dielectric Properties of Biological Substances at Radio and Microwave Frequencies-A Review", IEEE Transactions on Instrumentation and Measurement (vol. 29, Issue: 3, Sep. 1980), 9 pages.

Harney, William et al., "Electromagnetic Level Indicating (EMLI) System Using Time Domain Reflectometry", OCEANS '83, Proceedings, Aug. 29 Sep. 1, 1983, 4 pages.

"International Search Report and Written Opinion", Patent Cooperation Treaty Application No. PCT/US2019/027327, dated Jul. 10, 2019, 9 pages.

Cargol et al., "A Novel Method for FR Tomography and Acquiring Dielectric Signatures for Security Applications," IEEE, Nov. 2019, 4 pages.

* cited by examiner

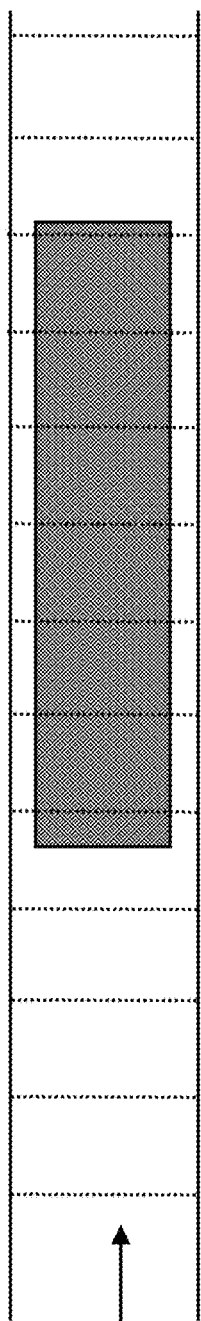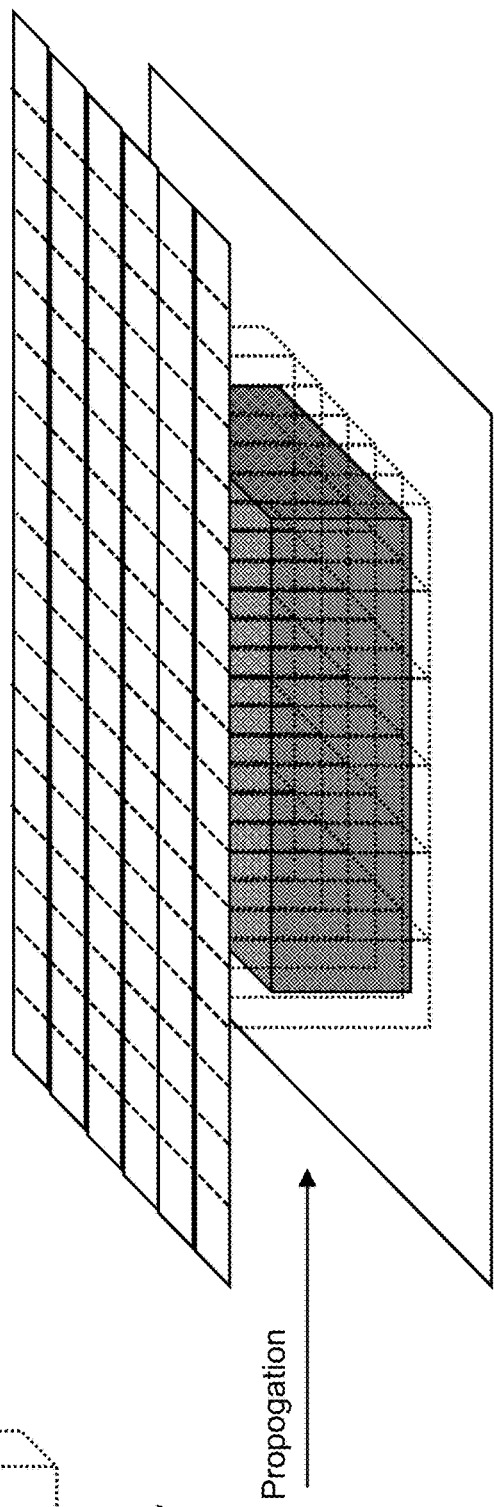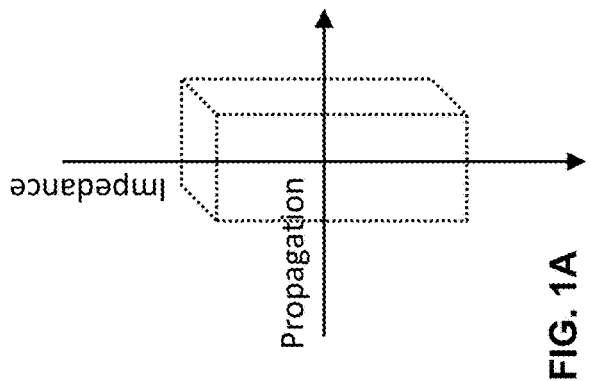

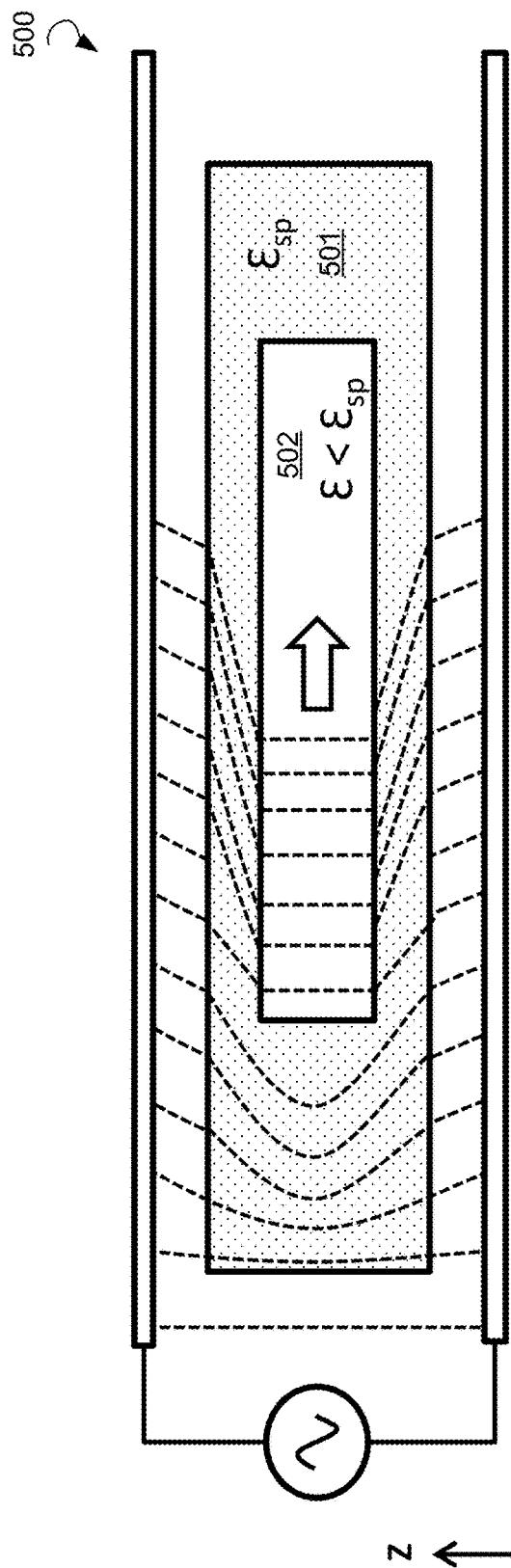
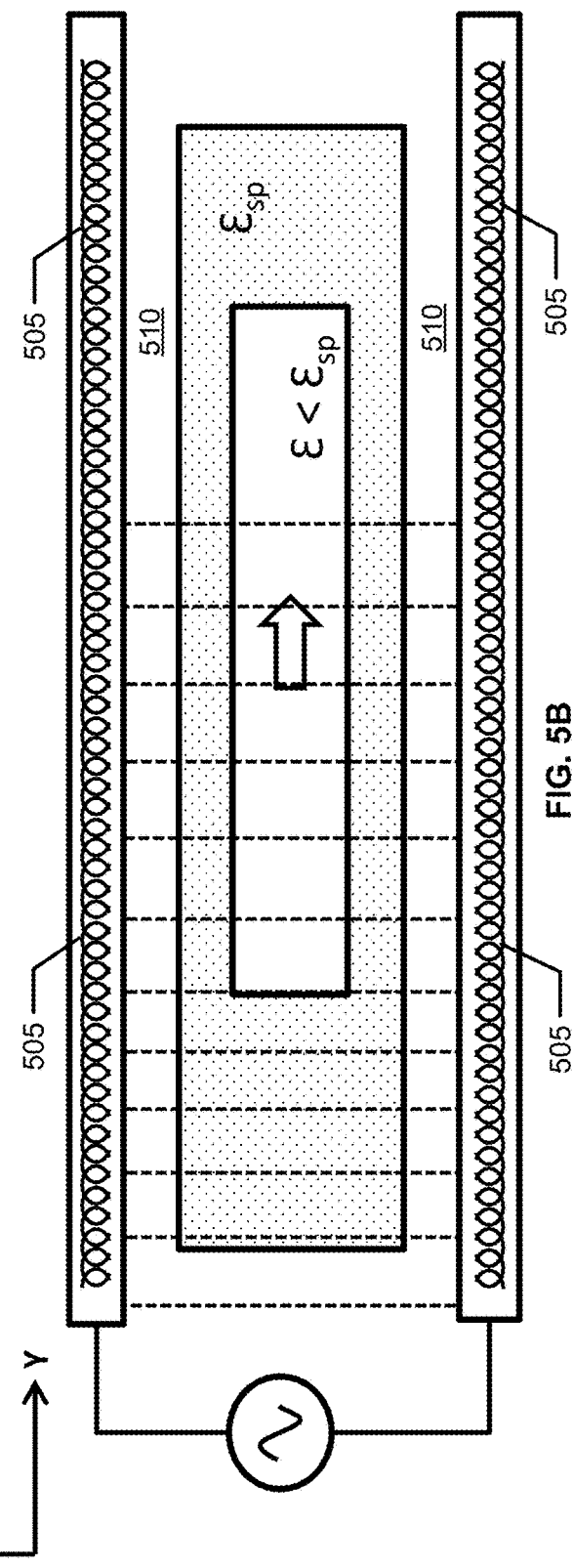
FIG. 5A
FIG. 5B

TOMOGRAPHIC SYSTEMS AND METHODS FOR DETERMINING CHARACTERISTICS OF INHOMOGENOUS SPECIMENS USING GUIDED ELECTROMAGNETIC FIELDS

RELATED APPLICATIONS

This patent application claims priority to and benefit of U.S. Provisional Patent Application Ser. No. 62/662,594, filed Apr. 25, 2018, titled "Tomographic Systems and Methods for Determining Characteristics of Inhomogenous Subjects Using Guided Electromagnetic Waves" and U.S. Provisional Patent Application Ser. No. 62/781,846, filed Dec. 19, 2018, titled "Method to Localize Measurement of Dielectric Characteristics to a Region within Inhomogeneous Dielectrics." The aforementioned disclosures are hereby incorporated by reference herein in their entireties including all references cited therein.

FIELD OF INVENTION

The present technology pertains to interrogation systems for determining characteristics and/or contents of subjects. In particular, but not by way of limitation, the present technology provides interrogation systems for determining characteristics and/or contents of dielectric specimens.

BACKGROUND

The approaches described in this section could be pursued, but are not necessarily approaches that have previously been conceived or pursued. Therefore, unless otherwise indicated, it should not be assumed that any of the approaches described in this section qualify as prior art merely by virtue of their inclusion in this section.

Electrical impedance, electrical capacitance, and microwave tomography have the potential to become powerful tools in the fields of medicine, security, and manufacturing and other fields that would benefit from the wealth of diagnostic information that can be gleaned from materials' dielectric properties. Unlike X-ray or ultrasound measurements that primarily indicate materials' density, dielectric properties can be unique to individual materials and can be used to, for example, identify specific tissues or tumors, or distinguish between explosives and foodstuffs. To date, these dielectric imaging techniques have found limited use in boutique diagnostics or in specific situations that permit dielectric measurements to be made.

Materials' dielectric properties are not readily resolved to specific spatial regions because dielectric structures can bend, contort, reflect, and diffract the propagation of electromagnetic fields in non-linear ways, which obscures both their spatial position and underlying dielectric characteristics.

The path of an electromagnetic field through a subject (i.e. specimen) under study will vary according to the frequency or, more generally, the rate of change of the field. In static conditions, or where wavelengths are an order of magnitude or more longer than the dielectric structures under investigation, the impedance characteristics of the subject under study will determine the paths of the current—fields will be drawn into the material of lowest impedance. As the frequency increases, however, propagation will take on more ray-like behaviors, and propagation will be dominated by the material of highest propagation velocity.

Traditionally, these two regimes are approached differently. Low-frequency or static techniques like electrical impedance tomography (EIT) or electrical capacitance tomography (ECT)—often called soft-field tomography because the bending and curving of the fields contrasts with the hard-field or straight line of X-rays through an object—apply an array of electrodes to the surface of an object under study and sequentially apply currents through pairs of electrodes to map out equipotential lines. A computer algorithm then iterates through the possible impedances of regions to match the equipotential curves measured in the data.

Low-frequency or static EIT/ECT fields can greatly obscure internal detail, especially at appreciable distance from a dielectric structure, because the fields tend to smooth out with distance. Static techniques also struggle with multi-layer structures—a key reason why EIT/ECT electrodes are directly applied to an object under study because an air gap would add a high impedance layer and impedance boundaries can obscure field structures within.

At much higher frequencies, techniques such as microwave tomography (MWT) use wavelengths similar to the size of the dielectric structures under study. At these frequencies, waves freely propagate and take on more ray-like characteristics. Although microwave paths can be more linear through some structures, they typically do not deeply penetrate subjects (i.e. specimens) of interest—such as the human body—and can dramatically diffract, reflect, and scatter around dielectric structures, creating a more dynamic inverse scattering problem than EIT/ECT, which can be more computationally demanding.

Although the scattering behaviors are different in the low-frequency/static and microwave regimes, both generate ill-posed scattering data that cannot be definitively inverted to resolve the spatial and electrical characteristics of the scattering dielectric structure. The data generated in both regimes can be cumbersome and time consuming to solve and may have multiple mathematically possible solutions or no solution at all.

Thus, two key problems have limited broad use of dielectric impedance tomography in three-dimensional, inhomogeneous, or complex high dielectric constant structures, such as the human body. The first is the significant mismatch between the dielectric characteristics of these structures and the surrounding air. The second is solving the inverse of multi-path or scattered electromagnetic waves through complex structures—a mathematically ill-posed problem.

The impedance mismatch between differing dielectric materials severely limits non-contact measurements because the majority of measuring electromagnetic waves will reflect or refract from the specimen of interest, and wavelengths that provide reasonable spatial resolution in air (typically GHz and above) are extremely dissipative in many high-dielectric-constant specimens. This limitation is currently addressed by either measuring impedances through direct contact with the specimen or performing measurements in a dielectric matching media. Such constraints are not practical in many situations where throughput and disruption are concerns, such as medical trauma, security, or manufacturing applications.

Even when spatially diverse data is obtained, solving the internal structure of inhomogeneous dielectrics can prove intractable when the probing electromagnetic waves are free to propagate, resonate, and interfere with each other. Although much literature has been devoted to studying this mathematical problem, significant computational resources may be required to develop even cursory solutions.

Several techniques have been proposed for tackling the inherent issues in dielectric impedance tomography. For example, several issued U.S. patents detail methods requiring a probe or array of probes to come into full contact with a patient or specimen. For example, see U.S. Pat. Nos. 9,042,957, 8,391,968, and 5,807,251.

Electrical impedance tomography methods that do not require specimen contact either require intermediate media or use very short wavelengths and high powers. Electrical impedance tomography methods that do not require specimen contact but require intermediate media are described, for example, in several issued U.S. patents including: U.S. Pat. Nos. 8,010,187, 4,135,131, 7,164,105, and 7,205,782. For example, electrical impedance tomography methods that do not require specimen contact but use very short wavelengths and high powers are described, for example, in several issued U.S. patents including: U.S. Pat. Nos. 8,933, 837, 7,660,452, and 7,664,303.

Capacitance measurement techniques or electrical capacitance tomography can offer advantages over impedance methods using freely propagating fields by completing a circuit between capacitor electrodes applied to the specimen. For example, systems that inherently use lower frequencies by constraining their propagation to the capacitor circuit for capacitive tomographic techniques are described, for example, in several issued U.S. patents including: U.S. Pat. Nos. 9,110,115 and 8,762,084. Although these techniques can reduce multi path complexity and attenuation of high frequencies, they require direct specimen contact and perform poorly in large or complex structures because electric fields are drawn to regions of a highest dielectric constant, looping around low dielectric constant regions or inhomogeneities, and potentially obscuring features of interest.

Where the dielectric profile to be studied extends only along a single dimension, transmission line methods have been successfully used. For example, in U.S. Pat. Nos. 9,074,922, and 4,240,445. See also, non-patent literature: *Open-wire Transmission Lines Applied to the Measurement of the Macroscopic Electrical Properties of a Forest region*, John Taylor, et al, Stanford Research Institute, October 1971; *Coaxial Line Reflection Methods for Measuring Dielectric Properties of Biological Substances at Radio and Microwave Frequencies-A Review*, IEEE Transactions on Instrumentation and Measurement (Volume: 29, Issue: 3, September 1980); and *Electromagnetic Level Indicating (EMLI) System Using Time Domain Reflectometry*, William J. Harney, Christopher P. Nemarich, Oceans '83, Proceedings, 29 Aug.-1 Sep. 1983.

There exists a need, therefore, for new systems and methods for tomographing dielectric materials that generate spatially solvable data and do not require excessively high frequencies, intermediate media, or intimate contact with the specimen under test.

Electromagnetic fields with linear or hard field characteristics would address these problems because they would yield tomographic data from a known and defined region. It is known that in a wave propagating in transverse electric (TE) or transverse electric and magnetic (TEM) modes, the electric fields are orthogonal to the direction of propagation. Therefore, if an electromagnetic field is propagating in a known direction and its propagation is determined to be in TE or TEM mode, linearity and direction of the electric fields can be assumed, creating a hard-field-like condition.

It is also known that in TE or TEM modes propagating through a media, propagation speed ($V_{prop}$) and impedance (Z) are related by the media's relative permittivity or dielectric constant ($\varepsilon_r$) as a component of its electric permittivity ($\varepsilon=\varepsilon_r \varepsilon_0$), such that:

$$\text{Impedance}(Z) = \sqrt{\frac{\mu}{\varepsilon}} \qquad (1)$$

$$\text{Speed}(V_{prop}) = \frac{1}{\sqrt{\varepsilon\mu}}$$

$$V_{prop} = \frac{1}{\varepsilon Z}$$

where $\mu$ is the material's magnetic permeability and $\varepsilon_0$ is the permittivity of free space. The above relationship holds in TE transmission in an inhomogeneous dielectric comprised of structures that are sufficiently small relative to the probing wavelength (or whose traversal time comprises an insignificant fraction of the probing frequency's period), that the dielectric behaves as a mixture or composite dielectric with linear contributions from the constituent dielectrics as formulated by others as:

$$\varepsilon_{eff} = \varepsilon_1 \left( \frac{\varepsilon_2}{\varepsilon_2 - f_2(\varepsilon_2 - \varepsilon_1)} \right) \qquad (2)$$

where $\varepsilon_{eff}$ is the effective dielectric constant of a mixture comprised of a first material with dielectric constant $\varepsilon_1$ and a second material of dielectric constant $\varepsilon_2$ comprising $f_2$ volume fraction of the mixture.

However, in an inhomogeneous dielectric with larger structures, speed and impedance may be dominated by the E of certain constituent physical elements of the structure. For example, if the traversal time through constituent dielectric structures differs by more than a small fraction of the probing frequency's period, the geometries and orientation of the constituent dielectric structures must be taken into account and the above mix equation is no longer accurate. Analytic equations for complex structures of significant frequency fractions in traversal time or more are complex, not readily solved, and often do not have unique solutions.

A practical example of this phenomenon is a foamed polyethylene (PE) coaxial cable: a homogenous foamed PE dielectric creates a transmission line (such as an RG-59 cable) of 75 Ohms and propagation velocity ($V_{prop}$) of 83% the speed of light. Whereas the same structure containing the same volume of air and PE, but concentrated into regions of pure PE and pure air, will have regional characteristics of 60 Ohms and 66% $V_{prop}$ for pure PE and 90 Ohms and 99% $V_{prop}$ for air. If these bifurcated regions are aligned along the direction of propagation, the differing propagation velocities will disrupt TEM behavior and the wave will encounter significant dispersion between the slower and faster dielectric components. From a measurement perspective, the line's impedance (or composite $\varepsilon_{eff}$) and propagation velocity will be a complex function of the probing frequencies and the PE and air constituent geometries.

If, in the above example, the line could be restored to TE mode, the effective dielectric constant $\varepsilon_{eff}$ can again become a linear function of the fraction of the constituent components such as Eq. 2 despite their bifurcation. This could be accomplished by inductively loading the center conductor of the coaxial cable to slow its velocity to match the slower solid PE constituent. An RG-63 coaxial cable is a practical manifestation of this behavior. By inductively loading the core conductor, RG-63 propagates in TEM mode with a uniform 125 ohms and 81% velocity despite containing a bifurcated PE and air dielectric along the direction of propagation.

SUMMARY

Various embodiments of the present technology include a system for determining characteristics of a specific region within an inhomogeneous dielectric specimen by guiding propagation of electric fields through the inhomogeneous dielectric specimen. In some embodiments the system comprises: (a) at least one source of electromagnetic energy for generating electromagnetic waveforms, the electromagnetic waveforms comprising electric fields propagating along a prescribed path that defines a series of spatial regions through which the electric fields propagate, the prescribed path comprising electric field modulating elements that determine a rate of electric field propagation along the prescribed path; (b) a plurality of conductors for guiding the electric field propagation through a inhomogeneous dielectric specimen in the prescribed path, the electric fields spanning between two or more of the plurality of conductors as the electric fields propagate along the prescribed path, the plurality of conductors being external to the inhomogeneous dielectric specimen; and (c) a plurality of measurement points for determining a measurement of the electric fields propagating along the prescribed path, the measurement of the electric fields used to determine regional dielectric characteristics of the inhomogeneous dielectric specimen and dielectric characteristics of the specific region within the inhomogeneous dielectric specimen.

In various embodiments the plurality of conductors for guiding the electric field propagation through the inhomogeneous dielectric specimen in the prescribed path comprise a first conductor parallel to a second conductor.

In some embodiments the plurality of conductors for guiding the electric field propagation through the inhomogeneous dielectric specimen in the prescribed path comprise an array of parallel conductor pairs. In various embodiments each pair of the array of parallel conductor pairs are opposed on opposite sides of the inhomogeneous dielectric specimen. In some embodiments each pair of the array of parallel conductor pairs are adjacent to each other on a same side of the inhomogeneous dielectric specimen.

In various embodiments the electromagnetic waveforms along the prescribed path are sequenced across the plurality of conductors, the sequenced electromagnetic waveforms being used to create a dynamic prescribed propagation path and a dynamic rate of electric field propagation.

In some embodiments the plurality of conductors for guiding the electric field propagation through the inhomogeneous dielectric specimen in the prescribed path comprise an array of discrete conductors. In various embodiments the electromagnetic waveforms along the prescribed path are sequenced across pairs of the array of discrete conductors, the sequenced electromagnetic waveforms used to create a dynamic prescribed propagation path and a dynamic rate of electric field propagation.

In various embodiments the electric field modulating elements that determine the rate of electric field propagation along the prescribed path comprise physical delay structures, the physical delay structures slowing the rate of electric field propagation along the prescribed path and decreasing a speed of electromagnetic waves along the prescribed path.

In some embodiments the electric field modulating elements that determine the rate of electric field propagation along the prescribed path comprise electronic components, the electronic components controlling the rate of electric field propagation along the prescribed path and controlling a speed of electromagnetic waves along the prescribed path.

In various embodiments the electric field modulating elements that determine the rate of electric field propagation along the prescribed path comprise active electronic components, the active electronic components generating electric fields to screen against parasitic effects.

In some embodiments the measurement of the electric fields propagating along the prescribed path measures one or more of: voltage, current, phase, and strength of the electric fields propagating along the prescribed path.

In various embodiments systems of the present technology further comprise: (d) at least one processor; and (e) a memory storing processor-executable instructions, wherein the at least one processor is configured to implement the following operations upon executing the processor-executable instructions: (i) determining an effective dielectric constant of the specific region within the inhomogeneous dielectric specimen; (ii) determining whether the effective dielectric constant of the specific region within the inhomogeneous dielectric specimen is consistent with the rate of the electric field propagation along the prescribed path; (iii) modulating the electric field propagation along the prescribed path when the effective dielectric constant of the specific region within the inhomogeneous dielectric specimen is not consistent with the rate of the electric field propagation along the prescribed path; (iv) measuring waveforms using the electric field propagation through the specific region within the inhomogeneous dielectric specimen; and (v) determining features of the specific region within the inhomogeneous dielectric specimen using the waveforms.

In some embodiments the at least one processor is further configured to implement the following operations upon executing the processor-executable instructions: generating a tomograph of the inhomogeneous dielectric specimen using the features of the specific region within the inhomogeneous dielectric specimen.

In various embodiments systems further comprise auxiliary sensors, the auxiliary sensors measuring an air gap between the plurality of conductors and the inhomogeneous dielectric specimen in the prescribed path.

In some embodiments the at least one processor is further configured to implement the following operations upon executing the processor-executable instructions: measuring the air gap between the plurality of conductors and the inhomogeneous dielectric specimen in the prescribed path; and adjusting the determining the effective dielectric constant of the specific region within the inhomogeneous dielectric specimen using the measuring the air gap to increase accuracy of the determining the effective dielectric constant.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and to explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

FIGS. 1A-C illustrate the concept of a region within which the present technology measures an effective dielectric constant $\varepsilon_{\mathit{eff}}$ according to various embodiments of the present technology.

FIGS. 5A-B illustrate the field behavior of an electromagnetic wave passing through an inhomogeneous dielectric, according to various embodiments of the present technology.

DETAILED DESCRIPTION

Figure 2:
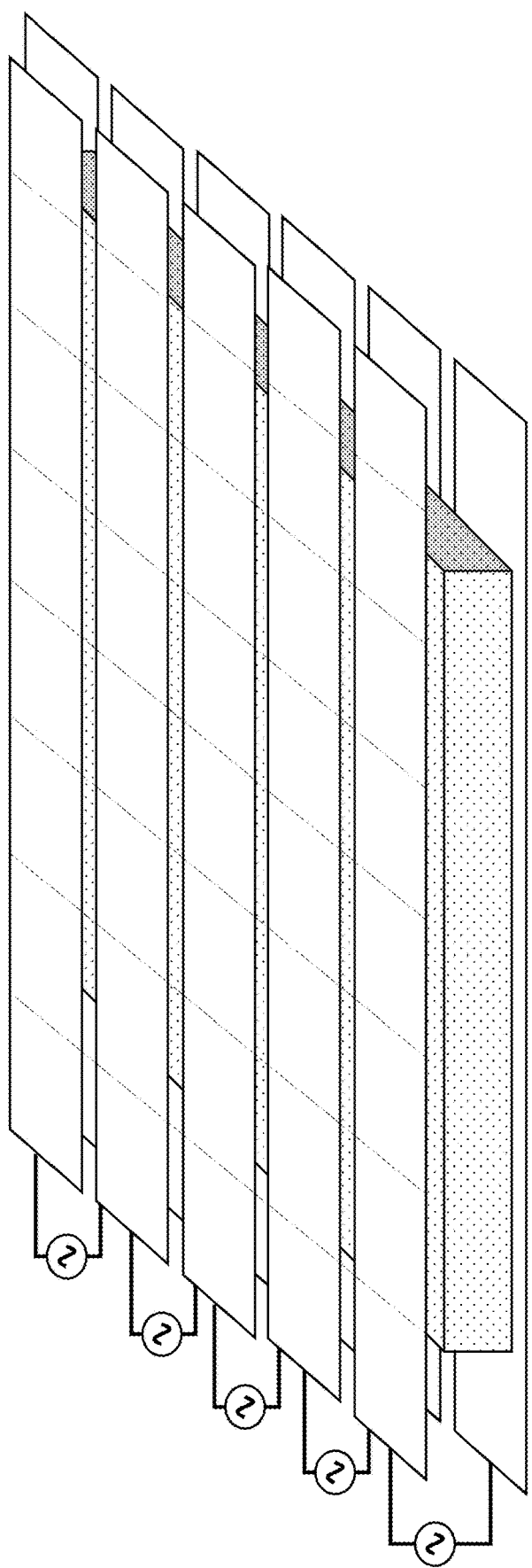
FIG. 2 illustrates an array of transmission line structures that define linear rows of regions along the path of propagation of each line, according to various embodiments of the present technology.

While the present technology is susceptible of embodiment in many different forms, there is shown in the drawings and will herein be described in detail several specific embodiments with the understanding that the present disclosure is to be considered as an exemplification of the principles of the present technology and is not intended to limit the technology to the embodiments illustrated.

In various embodiments the present technology provides a transmission line—like apparatus that spatially and temporally guides propagation of electromagnetic fields through an inhomogeneous dielectric specimen while providing external measurements points that reveal the dielectric's internal structure.

In various embodiments the present technology involves systems and methods to bring tractability to the dielectric impedance tomography problem by using external structures to guide the spatial propagation of electromagnetic fields, regulate their temporal velocity through a specimen, and provide a structure for external measurement on which internal dielectric features will manifest. When the electromagnetic field propagation is guided by a guiding external structure—such as a transmission line—the same impedance mismatches that complicate tomographic methods using freely propagating fields reveal and characterize different dielectric features of the specimens because perturbations induced by these internal dielectric features are externally measured along the guiding structure.

In various embodiments the present technology includes a pair of conductors or an array of conductor pairs along which an electric field propagates, with the conductors so arranged that the propagating fields between them pass through the specimen under test. The transmission line is driven by a radio frequency (RF) or pulse probing signal source as shown, and may or may not be terminated with a known impedance. In various embodiments, a field guiding system includes delay means for retarding the propagation of the probing signal so that the speed of propagation of the probing signal matches the speed of electromagnetic propagation within the specimen under test.

The present technology creates TE-like propagation within an inhomogeneous dielectric region under study so that the effective dielectric constant ($\varepsilon_{eff}$) of the region can be accurately determined. It accomplishes this by measuring the impedance between two conductive elements defining a region while also measuring and/or modulating the speed at which fields propagate through the region. Thus, the $\varepsilon_{eff}$ of a region is derived from two measurements: an impedance, and a propagation velocity at which the impedance was measured.

Figure 3:
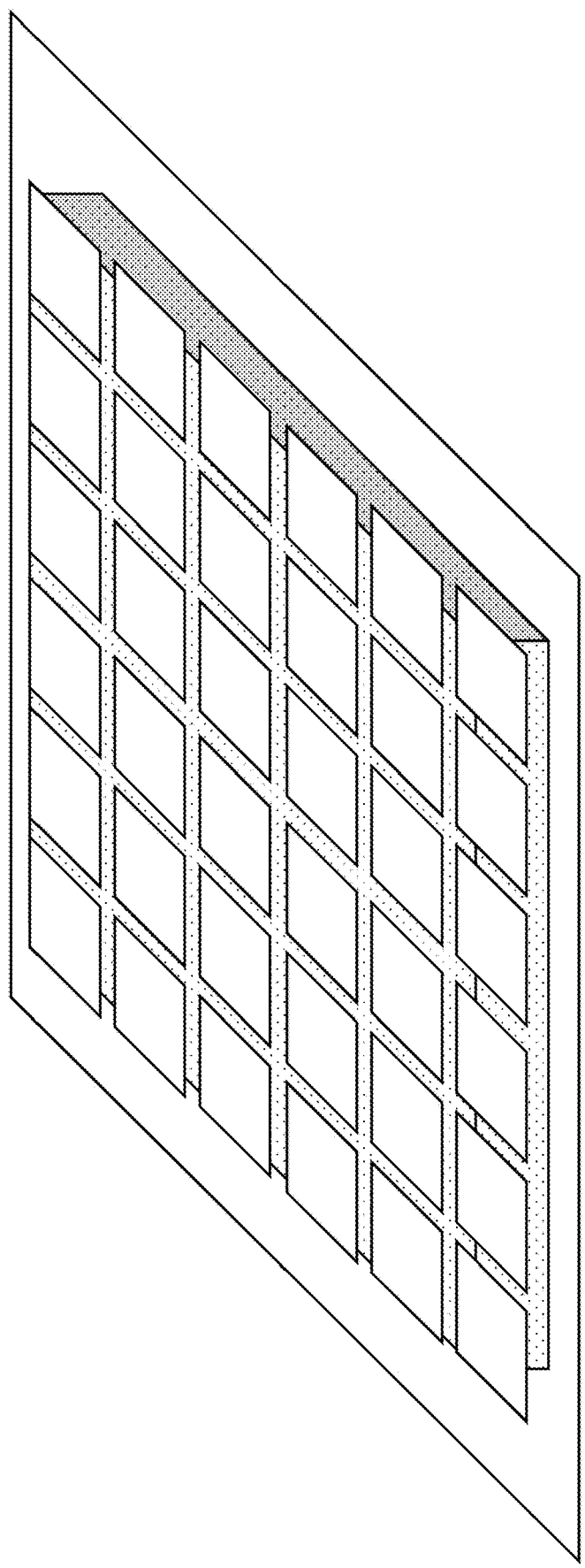
FIG. 3 shows a grid of metallic squares over a ground plane, each square defining a region through a dielectric specimen, illustrating a grid pattern of regions, according to various embodiments of the present technology.
Figure 9:
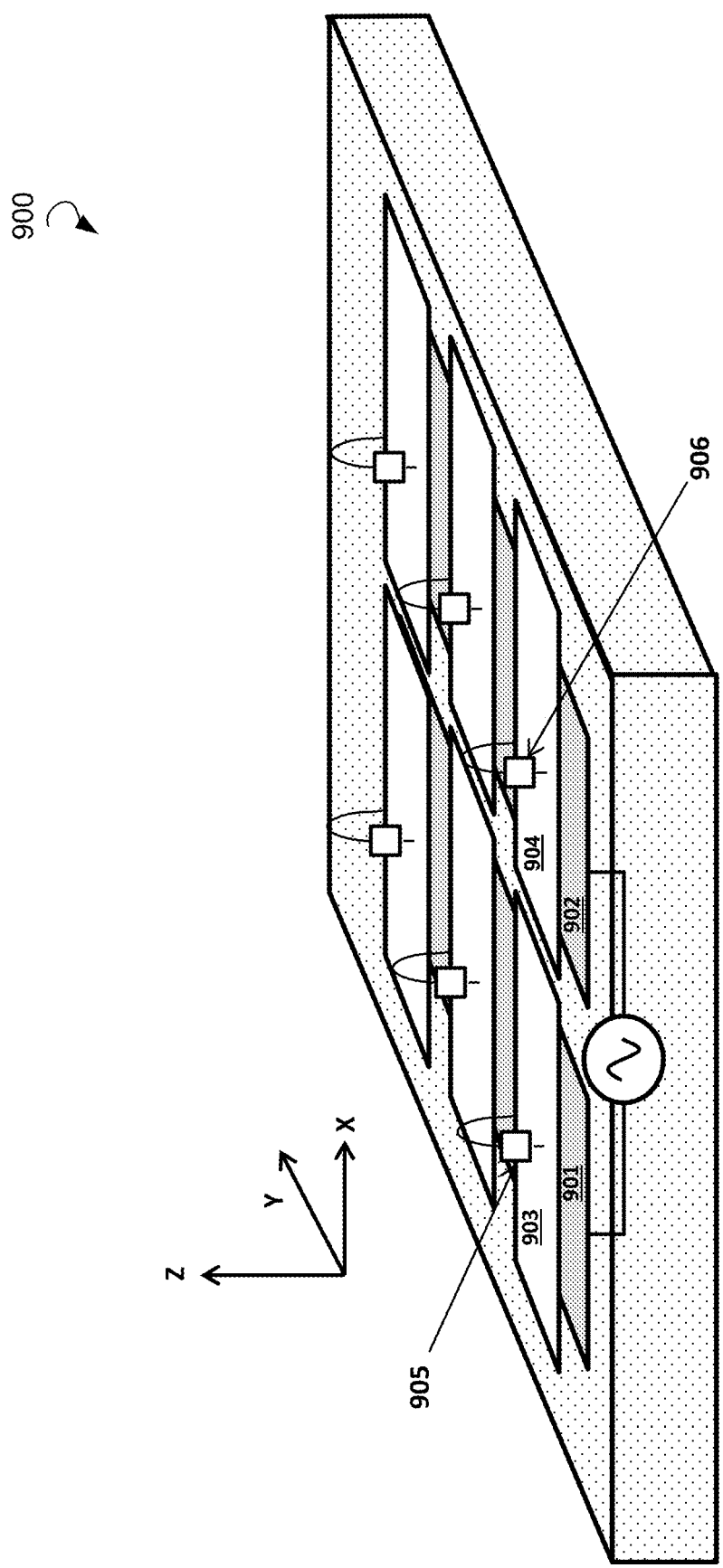
FIG. 9 illustrates a diagrammatic view of a system that includes a parallel transmission line structure applied to a surface of a specimen and screened by screening plates and driven by active elements according to embodiments of the present technology.
Figure 14:
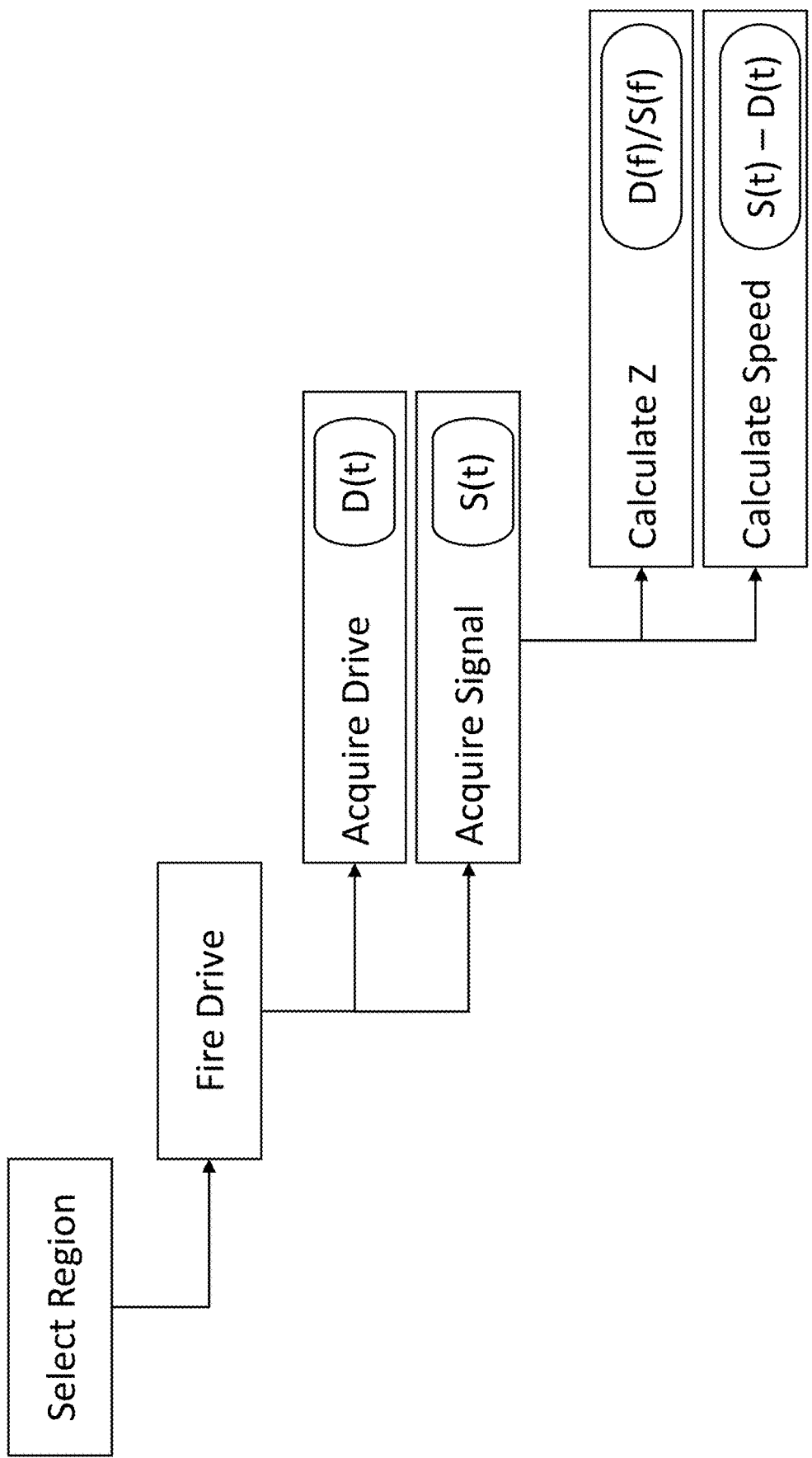
FIG. 14 shows a notional sequencing that the control and analysis computer of FIG. 13 would issue, according to various embodiments of the present technology.
Figure 15:
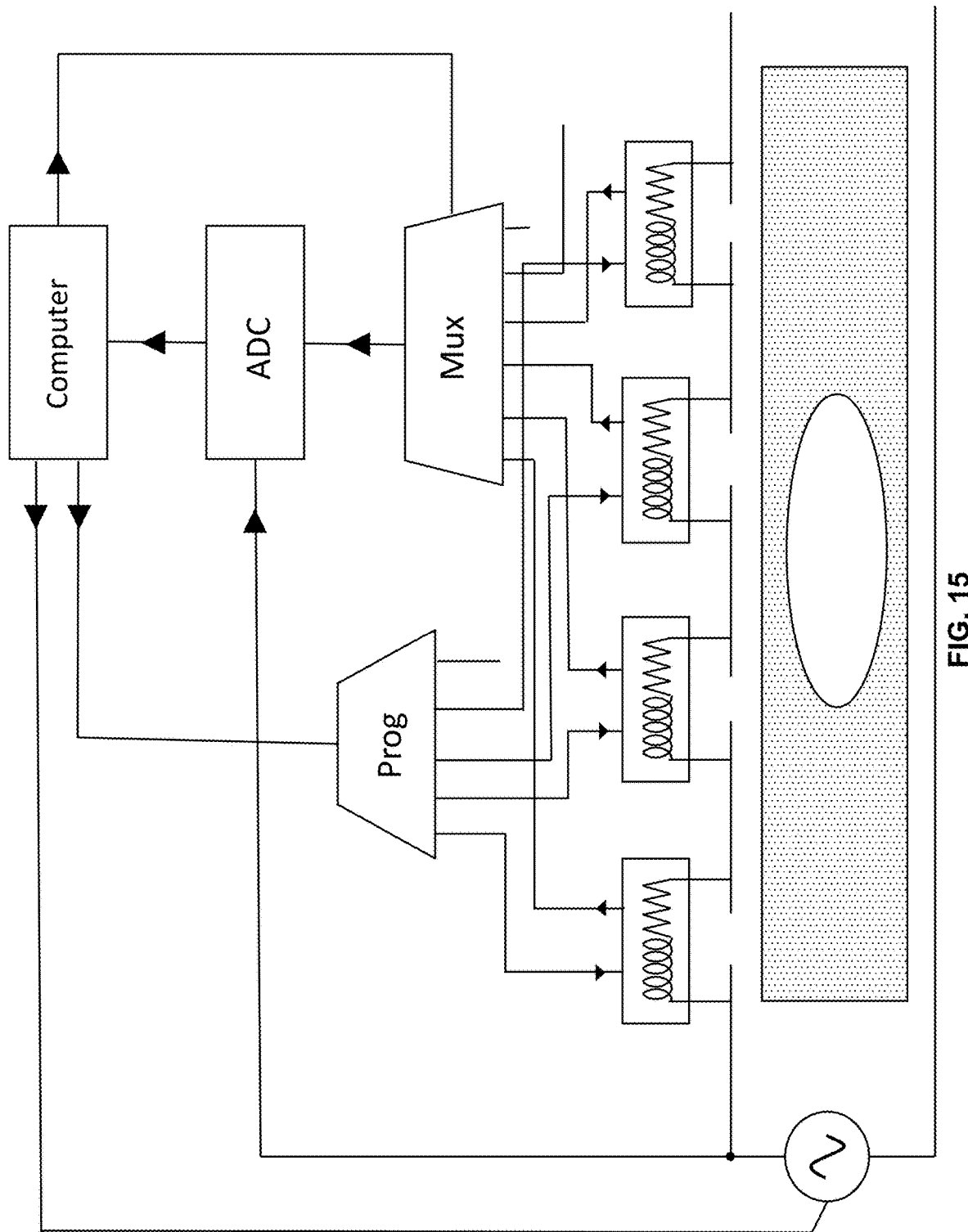
FIG. 15 illustrates the conceptual layout of hardware along the length of a single programmable transmission line, similar to the passive line, but incorporating a programmable element for each region, according to various embodiments of the present technology.

A spatial region for study is typically defined as a columnar region between two conducting plates as shown in FIGS. 1A-C. Impedance will be measured between the two plates, and the velocity of electromagnetic propagation through the region is determined either passively, as in transmission line-based embodiments, or in active embodiments, modulated to a prescribed value. Regions may be aligned along lengths of parallel transmission lines, as shown in FIG. 2, to spatially define the path for propagation from one region to the next, or they may be physically separate elements with a dynamically determined propagation pathway, as shown in FIG. 3. Propagation from region to region may be a passive process as in the case of a transmission line, or an active process where phased drive circuits propagate fields from one region to the next. Regions in either active or passive embodiment may be defined over a single ground plane as shown in FIGS. 2 and 3, with opposing elements as shown in FIGS. 14 and 15, or along a single side of a specimen as shown in FIG. 9.

In either the passive or active embodiments, the present technology determines the $\varepsilon_{eff}$ within the region by calculating a value from the impedance as measured by electronics probing voltage, current, and/or phase information for a specific region. Where the impedance is measured by a displacement current through a region, the $\varepsilon_{reff}$ of the region can be calculated as:

$$\varepsilon_{eff} = \frac{I(\omega)}{E(\omega)\omega} \frac{d}{A} \quad (3)$$

Where $I(\omega)$ is the measured current at a frequency ($\omega$) for an excitation $E(\omega)$ across a region of A area and d length. Alternative measurements of voltage across a region or current between regions will yield similar formulations with the premise of deriving the dielectric constant of the region based on voltage and current measurements made.

Likewise, the $V_{prop}$ can be taken as a function of the region's length in the direction of propagation and the field's transit time:

$$V_{prop} = \frac{\Delta t}{\Delta d}$$

Where $\Delta t$ is the propagation time from region to region, either as measured or as actively modulated by the system, and $\Delta d$ is the length of the region in the direction of propagation.

Figure 4:
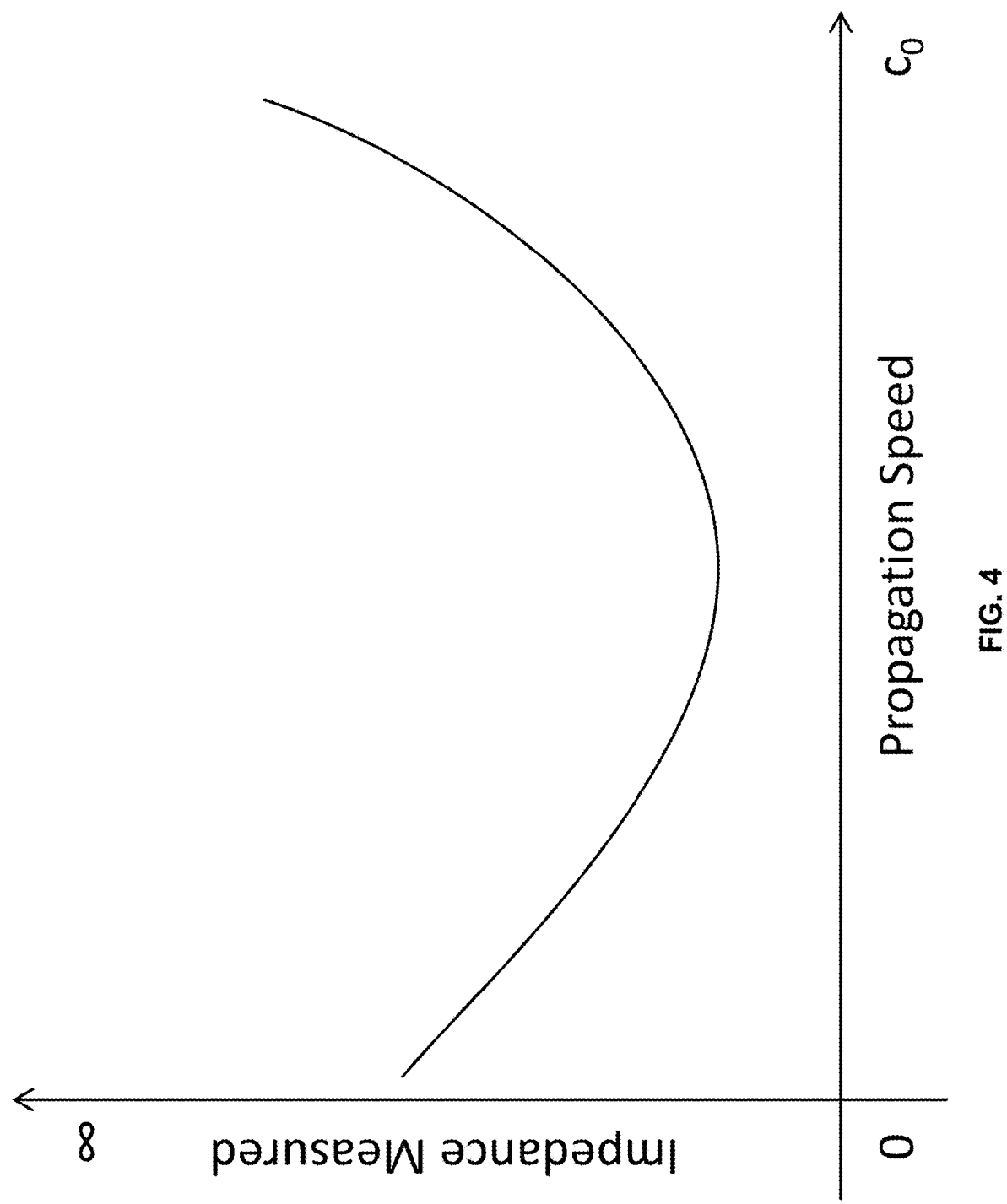
FIG. 4 notionally illustrates the impedance measured through a region of inhomogeneous dielectric as measured at various propagation speeds, according to various embodiments of the present technology.

The impedance measured within a region will vary depending on the speed at which the probing field traverses it, as illustrated in FIG. 4. At the characteristic speed of the $\varepsilon_{eff}$, the impedance will be at a minimum. However, if the propagation speed is faster than $\varepsilon_{eff}$, impedance will increase, because the fields will not have time to fully interact with the slower, low-impedance dielectric components. Likewise, if the speed of propagation from region to region is too slow, impedance will also increase, because the fields from previous regions will race out from their intended region and undercut into the region ahead. In general, a region's impedance will be at a minimum when its speed is properly matched to the intrinsic velocity of electromagnetic propagation of the region.

To obtain an accurate value for a region's $\varepsilon_{eff}$, it must be measured at multiple propagation speeds. This can be done by slowing the $V_{prop}$ by adding inductive, electronic, or other slowing mechanisms so that the $V_{prop}$ matches that of a region's slowest dielectric component, as shown in FIGS. 5A-B, to establish a TE mode. Additionally, slow wave or metamaterial structures such as electronic band-gap structures can be used to delay field propagation.

In one sense, these slowing mechanisms alter the fast dielectric components to form a virtual dielectric whose speed matches that of the slow dielectric component, thereby enabling a TE-like mode of propagation through the region. FIGS. 5A-B illustrate diagrammatic views 500 of propagation of electric fields at different velocities according to embodiments of the present technology. FIG. 5A shows propagation of an electric field through a transmission line running faster than a velocity of propagation in a dielectric under examination 501 (i.e., specimen), having dielectric constant $\varepsilon_{sp}$, thus obscuring an internal feature of the specimen 502, having dielectric constant $\varepsilon < \varepsilon_{sp}$. In contrast, FIG. 5B shows propagation of an electric field when a transmission line is slowed to accommodate an effective dielectric constant of a specimen, an internal feature of the specimen, and a surrounding air gap, thus, allowing the electric field a representative interaction with the dielectric. In more detail shown in FIG. 5B, the wave front through a specimen is slowed by distributed inductive elements 505 to accommodate the $\varepsilon_{eff}$ of the specimen, an internal feature, and a surrounding air gap 510, thereby creating a TE-like propagation mode and gaining a more fulsome and representative field interaction with the dielectric.

The velocity or propagation through a transmission line is a function of the per unit length capacitance ($C_{tl0}$) and inductance ($L_{tl0}$) such that:

$$V\text{prop}_{tl} = 1/\sqrt{L_{tl0}C_{tl0}} \quad (4)$$

A transmission line's $C_{tl0}$ is a function of line geometry and the $\varepsilon$ of its internal dielectric. The above formulation of transmission line velocity of propagation equation (4) mirrors that of the intrinsic velocity of a dielectric's electromagnetic propagation in equation (1), with the exception that per unit length characteristics of transmission line propagation are determined by physical structures and can therefore be manipulated. Therefore, by adding a per unit length inductive load or resistance $L_{L0}$ so that:

$$V\text{prop}_{tl} = \frac{1}{\sqrt{(L_{tl0} + L_{L0})C_{tl0}}} \cong V\text{prop}_s \quad (5)$$

where $V\text{prop}_s$ is the speed of electromagnetic propagation in the specimen region of interest, a TE-like mode can be obtained as shown in FIG. 5B.

Figure 7A:
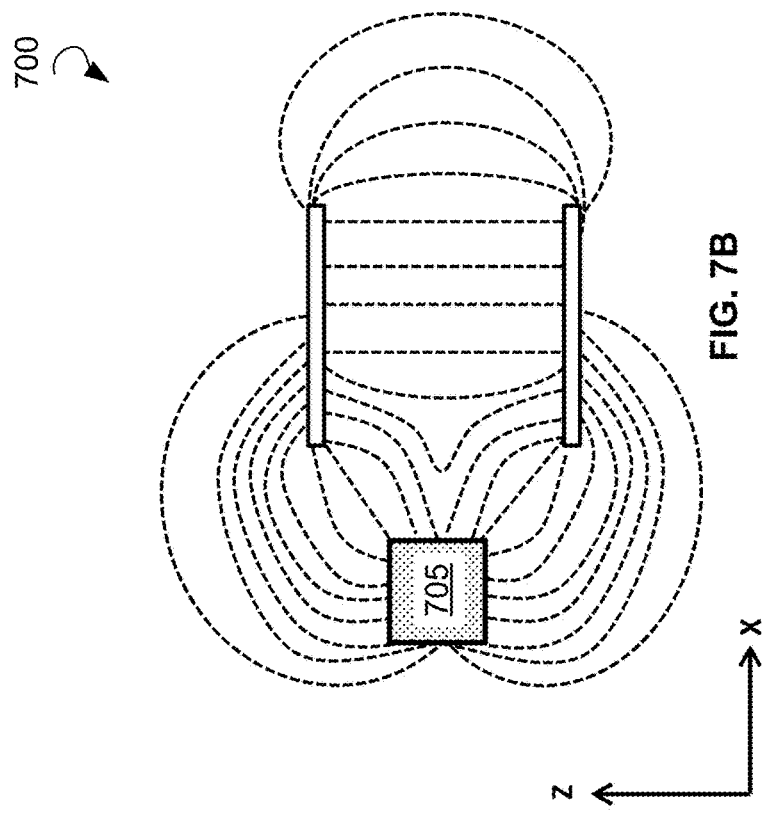
FIGS. 7A-D illustrate diagrammatic views of electric fields and regions measured for various screened and unscreened transmission lines according to embodiments of the present technology.
Figure 7B:
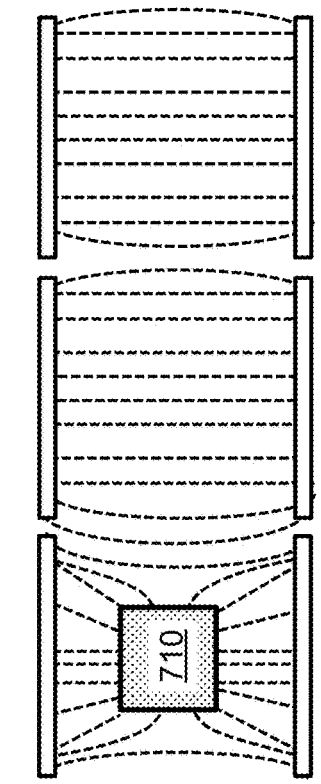
Figure 7C:
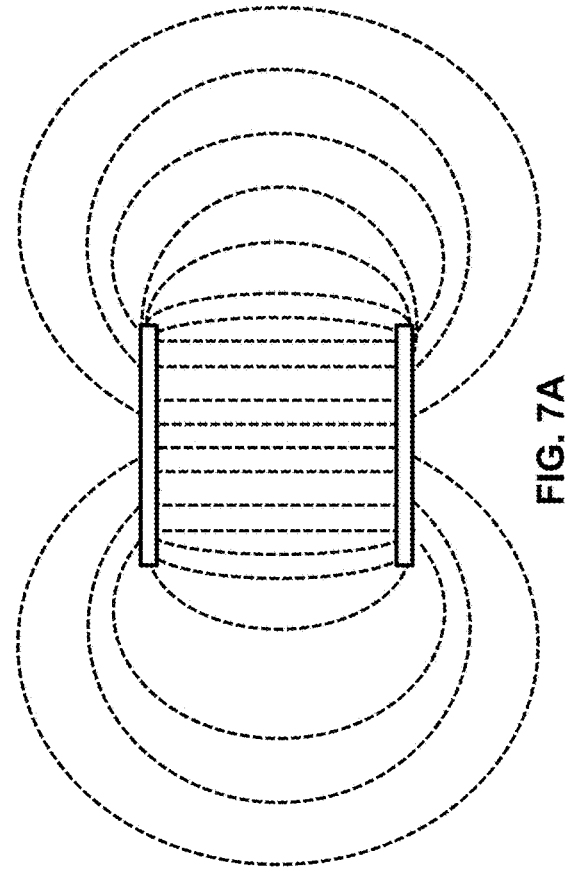
Figure 7D:
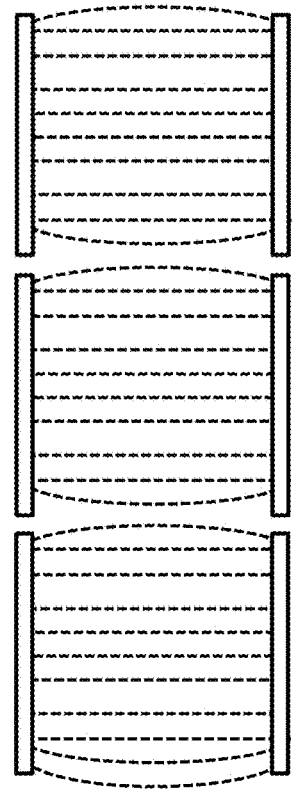

FIGS. 7A-D illustrates diagrammatic views 700 of electric fields and regions measured for various screened and unscreened transmission lines according to embodiments of the present technology. FIG. 7A shows an unscreened transmission line, FIG. 7B shows an unscreened transmission line with an outside high $\varepsilon_r$ feature 705, FIG. 7C shows an screened central transmission line, and FIG. 7D shows a screened central transmission line with an inside high $\varepsilon_r$ feature 710, according to embodiments of the present technology. In more detail, the diagrammatic views 700 of FIGS. 7A-D show electromagnetic waves propagating on lines parallel to either side of a given line, which provide fields that screen or restrict the x-axis spread of a central line's fields, thereby creating a narrower or more focused region in the central line's x-axis. FIG. 7A shows an electric field (and equivalently the region measured) in an unscreened line. FIG. 7B shows an unscreened line with the outside high $\varepsilon_r$ feature 705. FIG. 7C shows fields in a central line screened by parallel counterparts. FIG. 7D shows unperturbed fields of a central line screened by parallel counterparts, one of which contains the inside high $\varepsilon_r$ feature 710 between the parallel counterparts.

Figure 8:
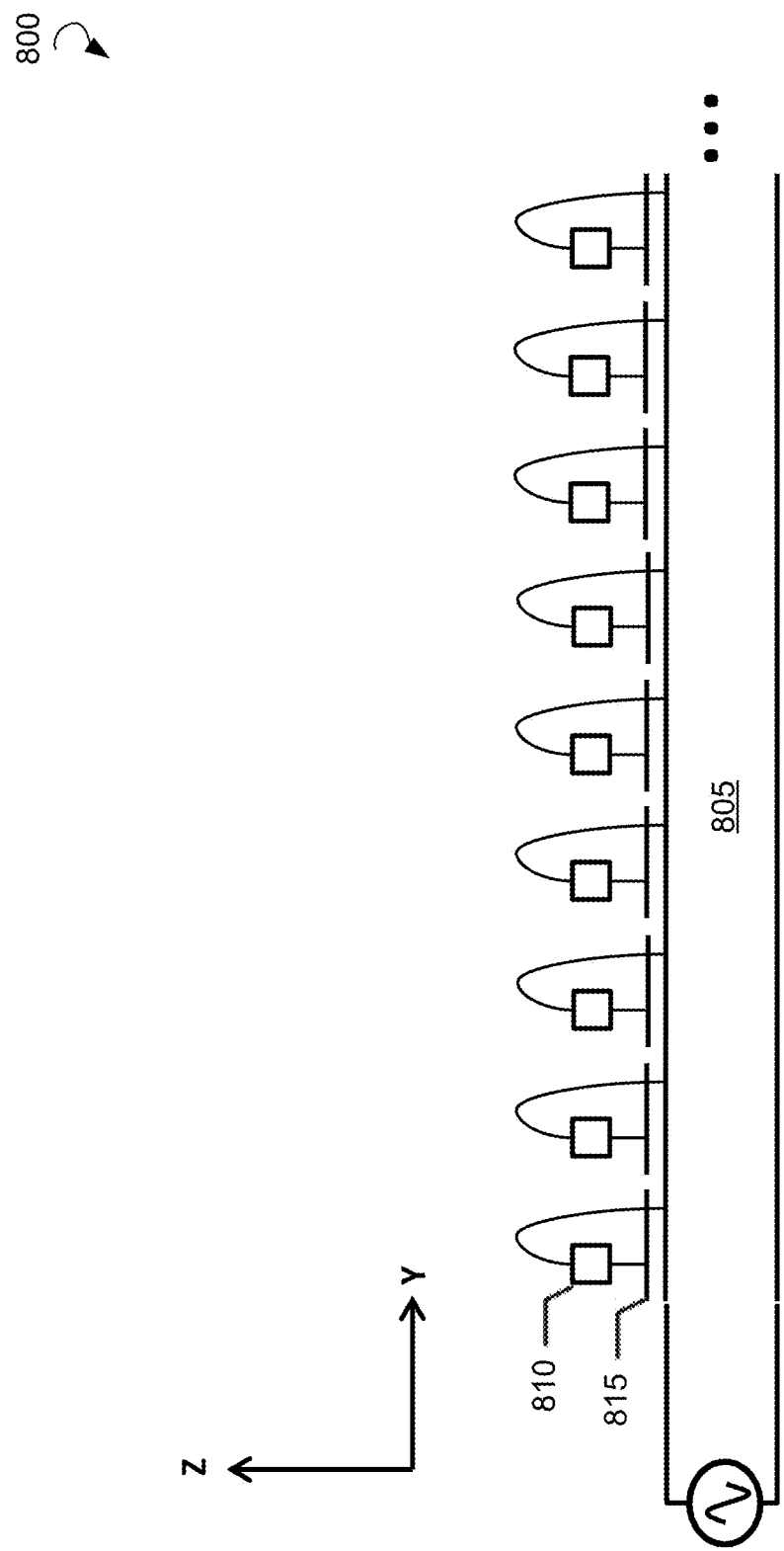
FIG. 8 illustrates a diagrammatic view of a system that includes a transmission line with screening plates driven by active followers according to embodiments of the present technology.

In various embodiments of the present technology a line's sensitivity may also be directed, for example, on a single line or to limit fields' z-axis spread above or below the specimen region—through the use of active screening elements as shown in FIG. 8. FIG. 8 illustrates a diagrammatic view of a system 800 that includes a transmission line with screening plates driven by active followers according to embodiments of the present technology. FIG. 8 shows system 800 comprising a guide structure 805 and screening plates driven by active followers. For example, screening plate 815 driven by active voltage follower 810. In this case, active components (e.g., active voltage follower 810) measure the voltage along the line as it changes with the propagation of a wave, and drive a plate (e.g., screening plate 815) or other radiating element to oppose fields radiating from the line in an undesirable direction. For example, in some embodiments the electric field modulating elements that determine the rate of electric field propagation along the prescribed path may comprise electronic components, the electronic components controlling the rate of electric field propagation along the prescribed path and controlling a speed of electromagnetic waves along the prescribed path. For example, in various embodiments the electric field modulating elements that determine the rate of electric field propagation along the prescribed path comprise active electronic components, the active electronic components also generating electric fields to screen against parasitic effects.

FIG. 9 illustrates a diagrammatic view of a system 900 that includes a parallel transmission line structure applied to a single surface of a specimen according to embodiments of the present technology. As in configurations where the parallel transmission lines are on opposing sides of the specimen, a region of characterization exists between the parallel conductors, but also extends both into the top layers of the specimen and air above the parallel lines. For example, each pair of the array of parallel conductor pairs may be adjacent to each other on a same side of the inhomogeneous dielectric specimen. FIG. 9 further shows active screening plates 903 and 904 and driving elements 905 and 906 applied to a parallel stripline 901 and 902 to screen the extent of the region of characterization from extending into the air above the parallel lines. Such an embodiment is used where only one side of the specimen is accessible or only a thin or top layer of an inhomogeneous dielectric need be characterized.

Figure 6:
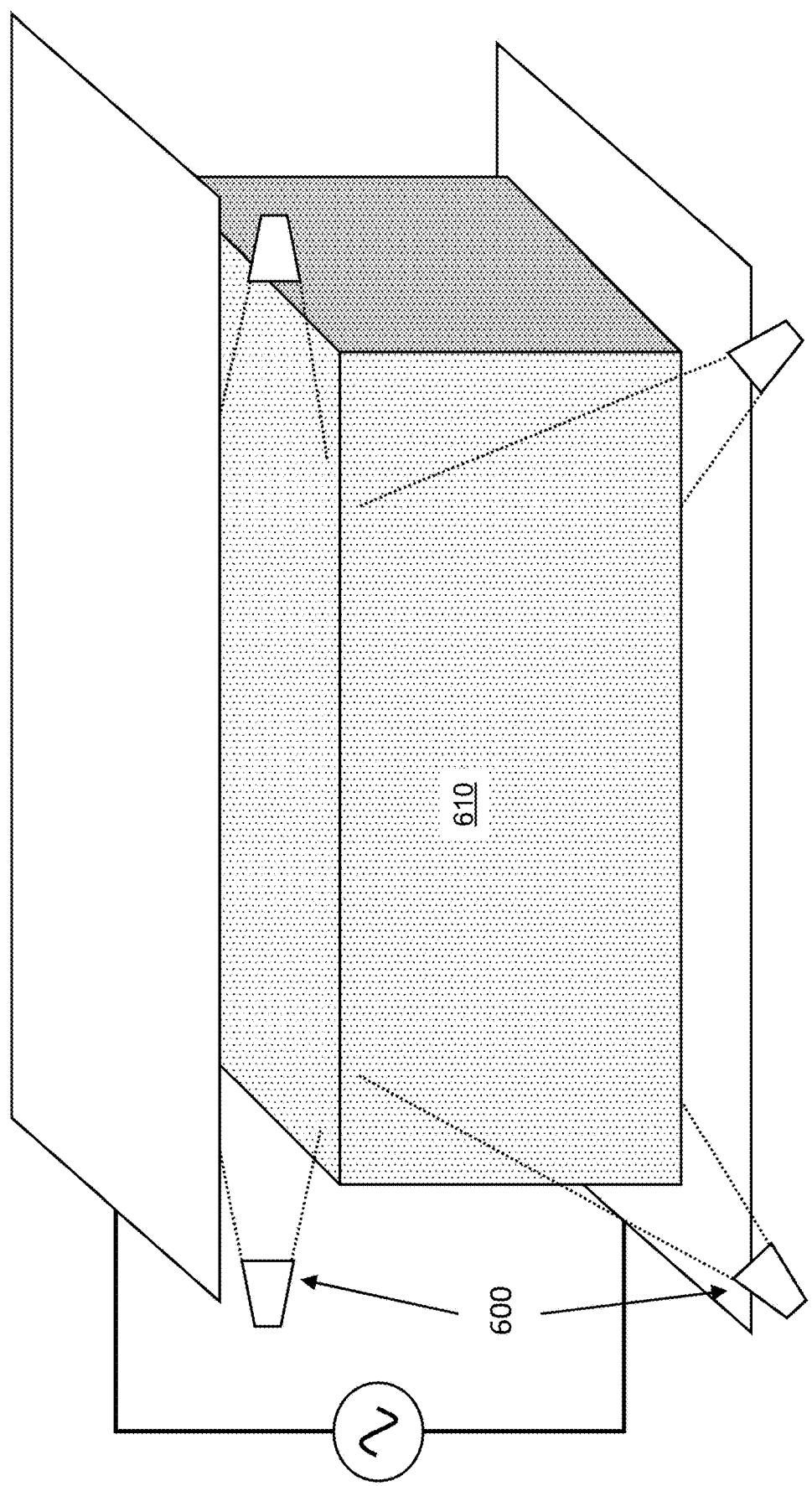
FIG. 6 illustrates four auxiliary sensors positioned to measure the air space between the region-defining structures and the specimen under study, according to various embodiments of the present technology.

Because the present technology may not involve contact with the specimen under study in various embodiments, accuracy may be further improved by incorporating ancillary sensors to determine the amount of air gap above or below the specimen within the region, as shown in FIG. 6. An air gap space (e.g., air gap 510) within a region but external to the specimen appears essentially the same if it were internal to the specimen. Advantageously, since a surrounding air space can be readily measured through other means (e.g., physical, optical, acoustical, etc.) its impact can be readily calculated out of the region's $\varepsilon_{eff}$ using mix equations like those of equation 2.

Figure 10:
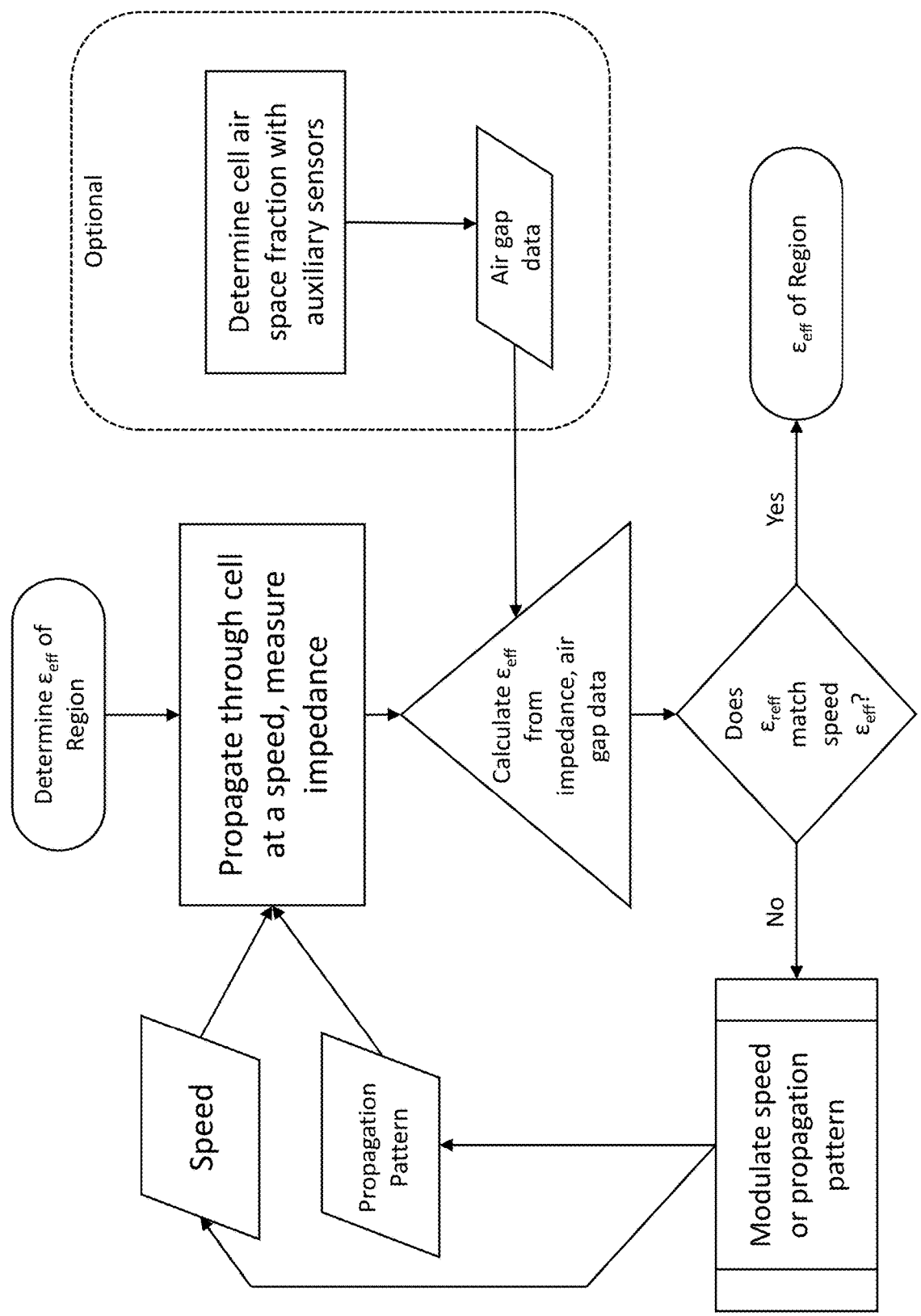
FIG. 10 illustrates a procedure to iteratively determine the $\varepsilon_{\mathit{eff}}$ of a specific region from a measured impedance and propagation velocity, according to various embodiments of the present technology.

A procedure for measurements to determine the $\varepsilon_{eff}$ of a region is described in FIG. 10 according to embodiments of the present technology. Propagation speed and propagation pattern can be passively, programmatically, or actively varied to fulfill the procedure described in FIG. 10. The procedure first determines a candidate $\varepsilon_{eff}$ through measurements and calculations like those of equation 3. The candidate $\varepsilon_{eff}$ is then evaluated as to whether it is consistent with the $V_{prop}$; i.e. whether the candidate $$\varepsilon_{eff} = \frac{1}{ZV_{prop}}, \text{ or } V_{prop} = \frac{1}{\varepsilon_{eff}Z} \qquad (6)$$

If $$V_{prop} < \frac{1}{\varepsilon_{eff}Z}$$

the candidate $\varepsilon_{eff}$ is too low and $V_{prop}$ is decreased to obtain a more accurate candidate $\varepsilon_{eff}$. The temporal and spatial pattern may be varied to optimally arrive at an optimal candidate $\varepsilon_{eff}$. Alternatively, a procedure might execute all possible combinations of speed and propagation pattern and then later evaluate the totality of data for the best candidate $\varepsilon_{eff}$.

Figure 11:
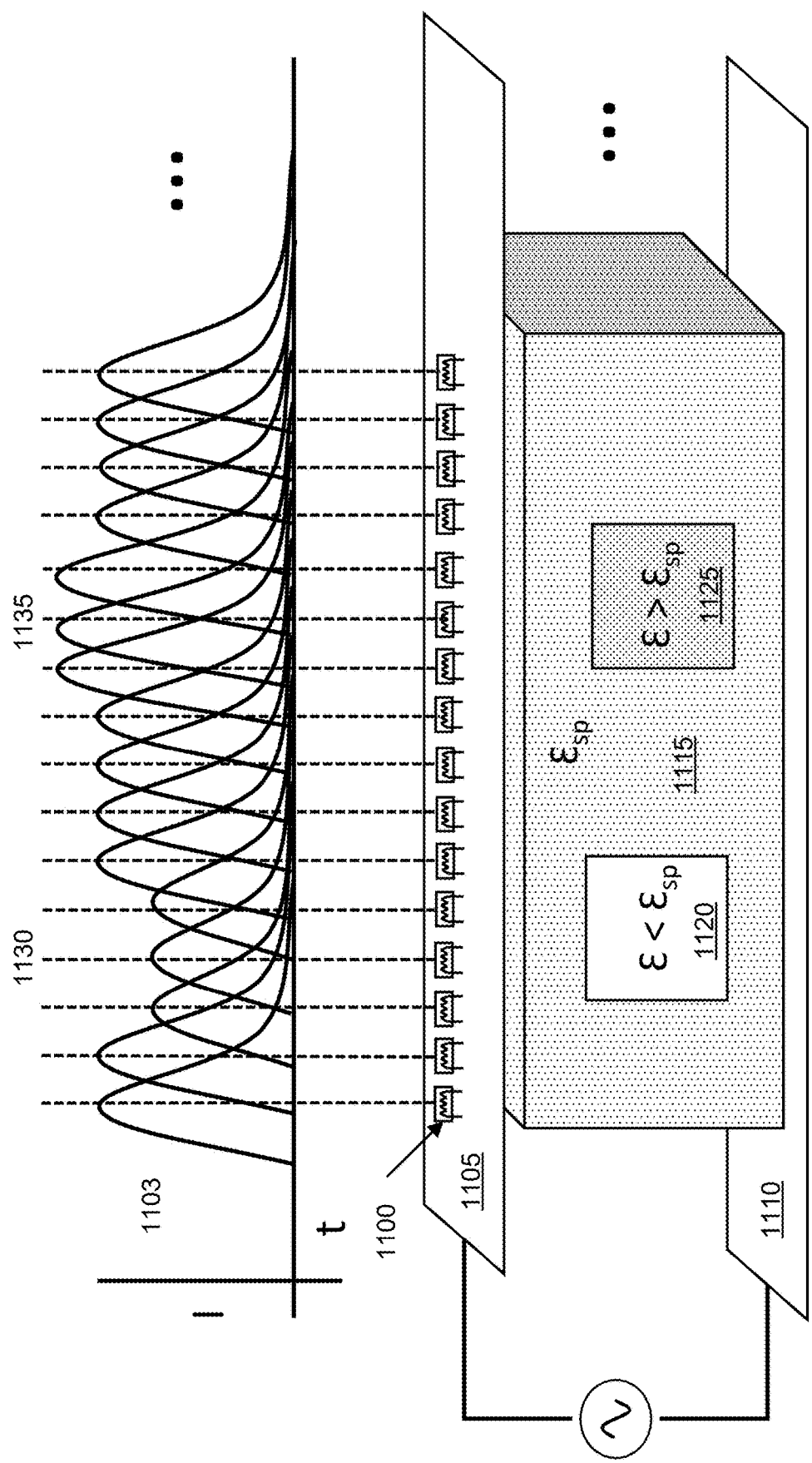
FIG. 11 illustrates the current through a transmission line structure as a pulse moves from region to region as measured by current-sensing elements, according to various embodiments of the present technology.

In a passive embodiment, several transmission lines are arrayed in parallel, as shown in FIG. 2, in order to laterally define rows of regions across the span of parallel transmission lines as shown in FIGS. 7C and 7D according to various embodiments. Regions are defined in the direction of propagation by points of measurement along the length of each line. The lines are driven by a radio frequency (RF) or pulse source probing signal and may or may not be terminated with a known impedance. As the RF or pulse signal propagates down the line, impedance changes will be revealed via voltage or current measurements on the surface of the line as shown in FIG. 11. Although these impedance changes will reveal the spatial location of dielectric structures, they may not fully reveal the $\varepsilon_{eff}$ of a specific region because the structures may have induced a non-TEM mode within the line, such as that shown in FIG. 5A. Obtaining measurements at points along the surface of the line which reveal impedance changes may be important to resolving the spatial uncertainty that arises from merely time domain reflectometry methods, where measurements made through an end port cannot disambiguate a short section of slow velocity dielectric from a long section of high velocity dielectric.

Passive line data at additional speeds can be obtained by inductively loading or altering an array of lines with slow wave structures as shown in FIG. 5B and equation 5. A further embodiment of FIG. 5B that affords a variety of propagation speeds is the array of parallel transmission lines shown in FIG. 12. Each line is structured to have a slightly different propagation velocity. The array is mechanically passed over the specimen and impedance data for each region is gathered when scanned by each line of different velocity. Comparing impedance data from lines of various speeds as they passed over the same physical region of the specimen can identify the minimum impedance value that matches a propagation velocity per equation 6 above.

Impedance is measured from each region of the passive embodiment via a voltage and/or current probe within the region according to various embodiments. Impedance is then calculated via Ohm's law by knowing the drive signal or signal from the previous adjacent region. The candidate $\varepsilon_{eff}$ is then calculated from the impedance of the line based on the physical bounds of the region and any added inductive or slowing structures. FIG. 13 shows the hardware of a preferred embodiment using a current sensor between regions. FIG. 14 shows a process for operation using a current sensor between regions as orchestrated by a controlling computer. The speed and impedance data generated by a single-speed line, as illustrated in FIG. 13, may be stored by the computer for comparison against speed and impedance data from varying speed lines, such as those from FIG. 12, to determine the optimal fit for $\varepsilon_{eff}$.

Figure 12:
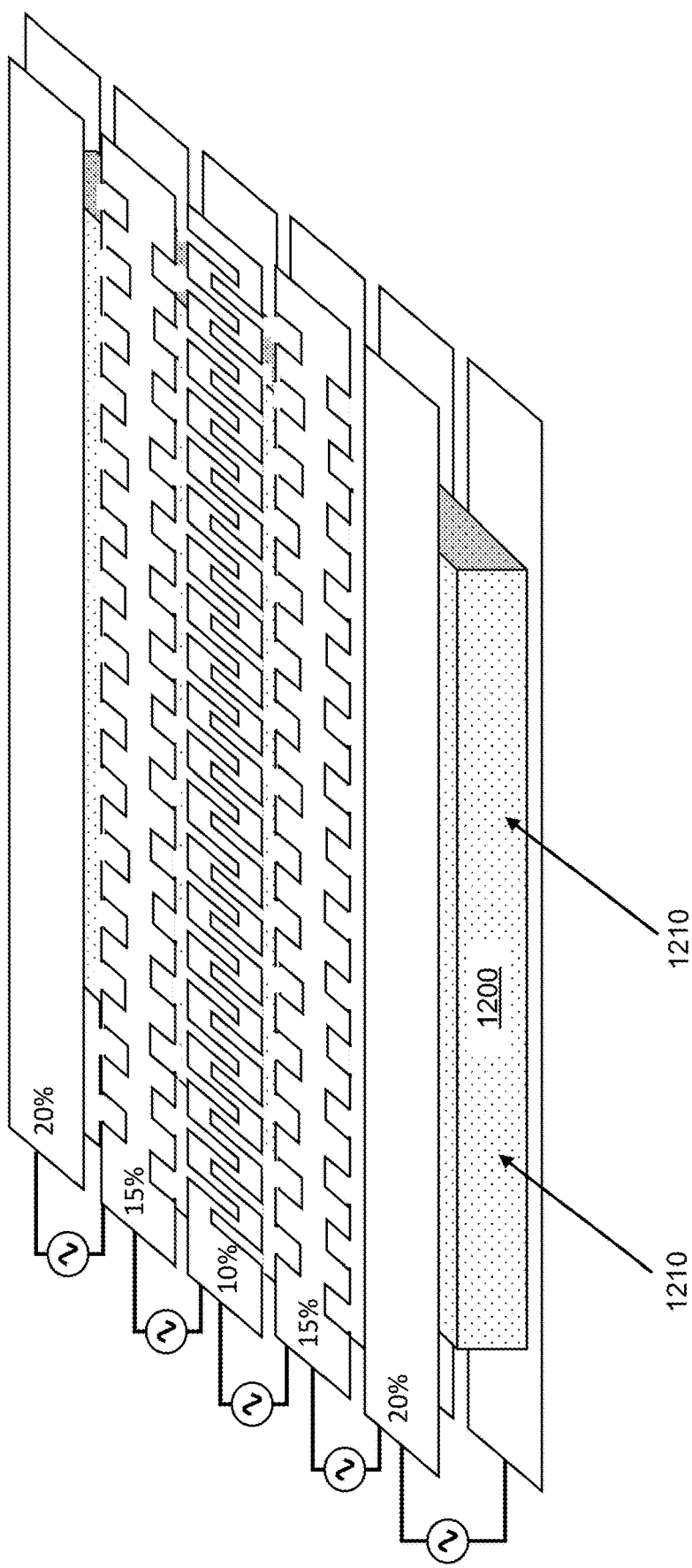
FIG. 12 illustrates an array of transmission line structures each inductively loaded or designed to propagate at a different speed and thereby measure the impedance of a region at a different speed, according to various embodiments of the present technology.
Figure 13:
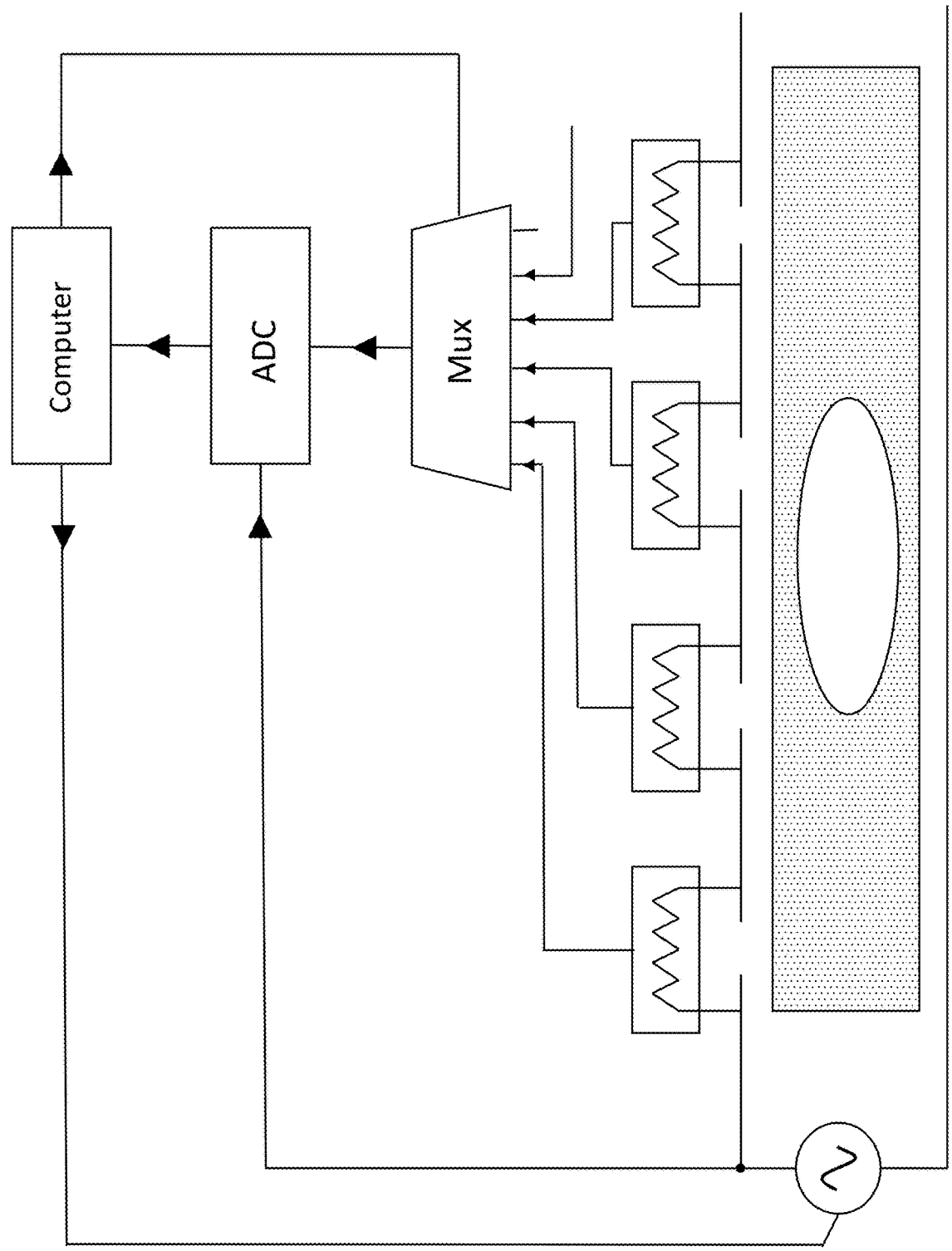
FIG. 13 illustrates the conceptual layout of hardware along the length of a single passive transmission line, according to various embodiments of the present technology.

An extension of the passive embodiment is a programmable embodiment where the inductive or delay elements between regions along a line can be altered or programmed to tune the line to a different speed, as illustrated in FIG. 12. A delay element, such as an inductor or programmable delay line, may be switched on or its characteristics altered as instructed by the control computer. For example, the electric field modulating elements that determine the rate of electric field propagation along the prescribed path may comprise physical delay structures, the physical delay structures slowing the rate of electric field propagation along the prescribed path and decreasing a speed of electromagnetic waves along the prescribed path.

In an active embodiment, field propagation from region to region is controlled by electronics and not free propagation as in the passive embodiment. Each region contains its own probing signal source controllable by a control and analyzing computer, as well as mechanisms for impedance measurement and/or waveform capture. In the active embodiment, the rate and direction of propagation from region to region is determined by a control and analyzing computer and may be dynamically or iteratively altered to determine a regions' $\varepsilon_{eff}$.

Figure 18:
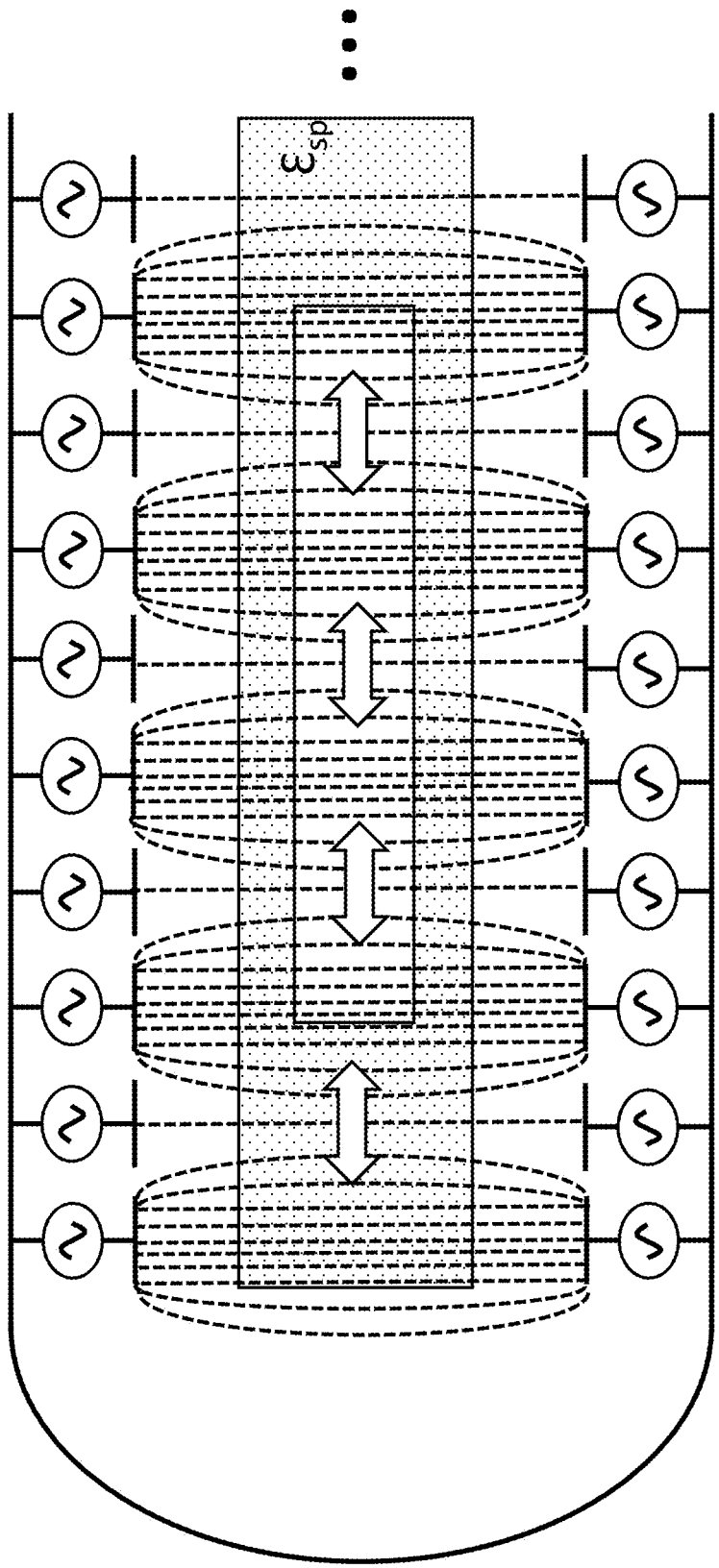
FIG. 18 illustrates the conceptual propagation of fields in a two-dimensional section of an active embodiment as the regional fields sources are sequenced in outward or radial patterns, according to various embodiments of the present technology.

Active regions may be defined by plates in a grid, hexagonal, arcs, or other repeating pattern as suited to the application. The propagation from region to region may likewise be altered to suit the application. Detection of boundaries between dielectric structures can be clearer when propagating from lower ε to higher ε, and propagation paths are normal to boundaries. Thus, a sophisticated active embodiment dynamically alters propagation paths and patterns to discern finer detail. For example, regions could propagate in one direction and then back, propagate radially or concentrically, diagonally across the scanning plane, or alternated or phased in a checkerboard pattern as shown in FIG. 18. In an active embodiment, propagation may be originated and terminated at various points. Active propagation also eliminates the need for mechanical operations, such as sweeping the varied speed lines embodiment of FIG. 12 or reorienting the specimen, to gather full tomographic data.

Figure 19:
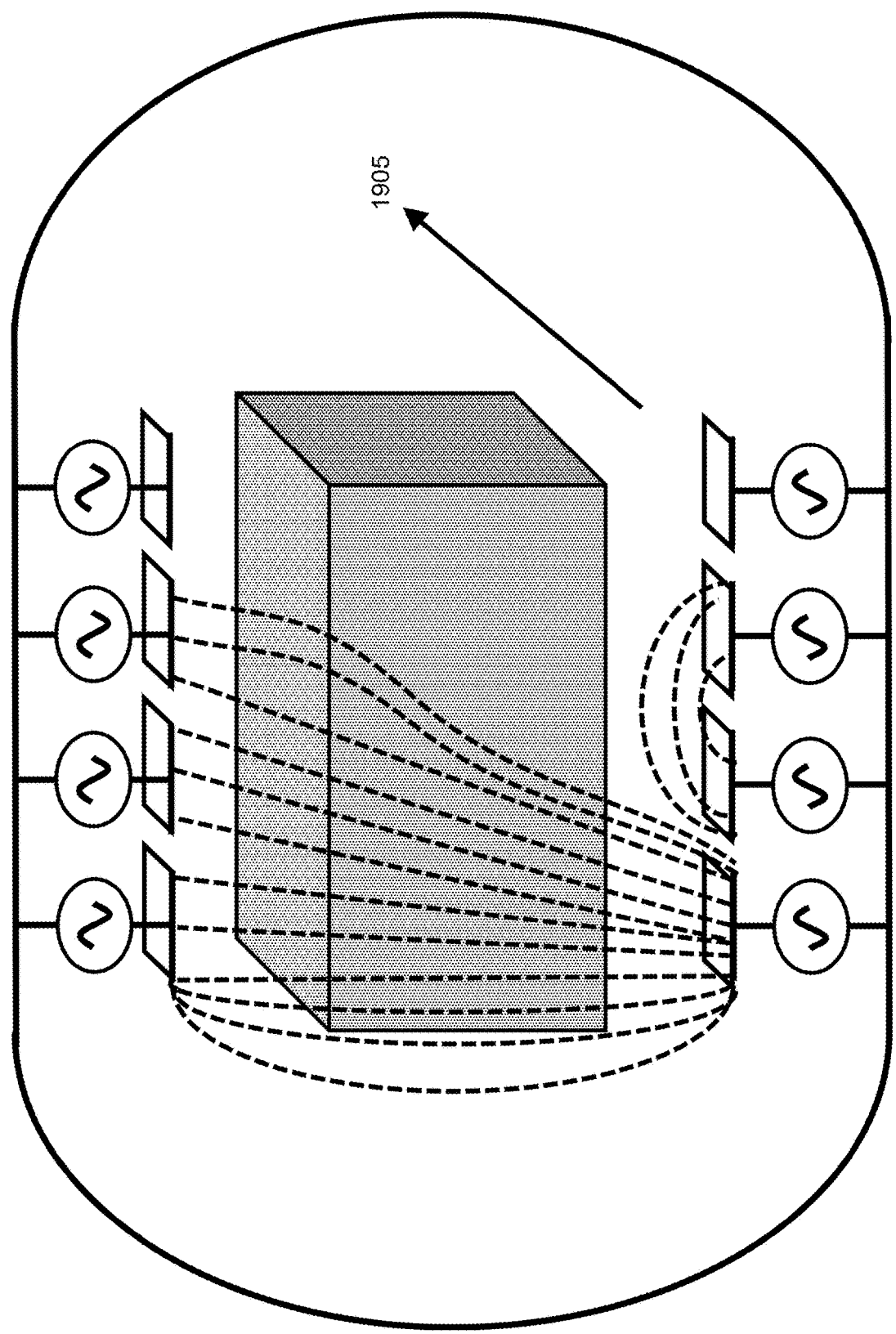
FIG. 19 illustrates the concept of region tilting by adjusting the field producing elements in an active embodiment such that the regions are angled from the lower left to upper right as they propagate into the page, according to various embodiments of the present technology.

All embodiments generate an $\varepsilon_{eff}$ of a columnar region which may still contain multiple dielectric components in the axis of the column. To resolve this uncertainty and generate a full tomographic rendering, data must be gathered from an orthogonal axis. In passive embodiments, this can be done by reorienting either the specimen or passive lines. In a two-sided active embodiment, alternate region axes can be obtained by tilting the regions through slight phasing of the top and bottom plates of the cell and/or creating a screening field though adjacent region plates as shown in FIG. 19, so long as the tilted region still approximates TE in the direction of propagation.

Those skilled in the art will appreciate that numerous modifications and variations may be made to the above disclosed embodiments without departing from the spirit and scope of the present invention.

FIGS. 1A-C illustrate the concept of a region within which the present technology measures an effective dielectric constant ($\varepsilon_{eff}$). Impedance through the region is indicated by currents passing vertically while fields are propagating to the right as depicted in FIG. 1, FIG. 1B, and FIG. 1C illustrate this conceptual region within transmission line structures in two dimensions and three dimensions, respectively. For example, the plurality of conductors for guiding the electric field propagation through the inhomogeneous dielectric specimen in the prescribed path may comprise a first conductor parallel to a second conductor.

FIG. 2 illustrates an array of transmission line structures that define linear rows of regions along the path of propagation of each line. For example, the plurality of conductors for guiding the electric field propagation through the inhomogeneous dielectric specimen in the prescribed path may comprise an array of parallel conductor pairs. In some embodiments each pair of the array of parallel conductor pairs are opposed on opposite sides of the inhomogeneous dielectric specimen.

FIG. 3 shows a grid of metallic squares over a ground plane, each square defining a region through a dielectric specimen, illustrating a grid pattern of regions. The grid of FIG. 3 depicts a lumped or segmented version of the continuous lines of FIG. 2. Adding connective elements between the squares in the vertical direction would allow electromagnetic fields to propagate from region to region vertically. Adding horizontal connective elements would allow fields to propagate horizontally, akin to the lines in FIG. 2.

FIG. 4 notionally illustrates the impedance measured through a region of inhomogeneous dielectric as measured at various propagation speeds. Where the propagation from region to region is too slow relative to the intrinsic of the dielectric, the impedance of the measured region is high due to undercutting of fields from earlier, adjacent regions. Where the propagation is fast, the impedance is again high because the fields do not have time to penetrate slower dielectric components.

FIGS. 5A-B illustrate the field behavior of an electromagnetic wave passing through an inhomogeneous dielectric. In FIG. 5A, the wave is moving at a velocity in excess of the propagation velocity of the slower dielectric component. In FIG. 5B, the transmission line structure has been slowed to allow the wave to propagate in a transverse electric (TE) mode.

In FIG. 5A, propagation of an electric field through a transmission is line running faster than a velocity of propagation in a dielectric under examination, thus obscuring an internal feature of the specimen. In contrast, FIG. 5B shows propagation of an electric field when a transmission line is slowed to accommodate an effective dielectric constant ($\varepsilon_{eff}$) of the dielectric under examination 501 (i.e., specimen), an internal feature of the specimen 502, and a surrounding air gap 510, thus allowing the electric field a representative interaction with the dielectric.

FIG. 6 illustrates four auxiliary sensors 600 positioned to measure air space between the region-defining structures and the subject 610 (i.e., specimen) under study. The auxiliary sensors may operate by radar, infrared, ultrasound, or optical/video means to quantify the amount of air space between the specimen and the region-defining structures. In various embodiments, the auxiliary sensors measure an air gap between the plurality of conductors and the inhomogeneous dielectric specimen in the prescribed path.

FIG. 10 illustrates a procedure to iteratively determine the $\varepsilon_{eff}$ of a specific region from a measured impedance and propagation velocity.

FIG. 11 illustrates the current through a transmission line structure as a pulse moves from region to region as measured by current-sensing elements 1100. FIG. 11 illustrates a diagrammatic view of measured pulse current waveforms in a system according to embodiments of the present technology. FIG. 11 shows pulse current waveforms 1103 as measured at points along the length of a first conductor 1105 and second conductor 1110. The first conductor 1105 and the second conductor 1110 encompass a specimen 1115 undergoing test that includes features of a lesser dielectric constant 1120 and features of a greater dielectric constant 1125 relative to a dielectric constant of the specimen 1115.

FIG. 11 also shows pulse current waveforms 1103 that have a lower current illustrating a valley 1130 on the pulse current waveforms 1103 corresponding with the features of lesser dielectric constant 1120. In contrast, pulse current waveforms 1103 have a higher voltage illustrating a peak 1135 on the pulse current waveforms 1103 corresponding with the features of greater dielectric constant 1125.

FIG. 12 illustrates an array of transmission line structures each inductively loaded or designed to propagate at a different speed and thereby measure the impedance of a region at a different speed. Such an array is passed over a specimen 1200 (i.e., specimen) under study as shown by direction 1210 to measure the same region of the specimen under lines of different speeds. For example, the electromagnetic waveforms along the prescribed path are sequenced across each pair of the array of parallel conductor pairs, the sequenced electromagnetic waveforms may be used to create a dynamic prescribed path for electric field propagation.

FIG. 13 illustrates the conceptual layout of hardware along the length of a single passive transmission line. Each region is defined by current sensing elements, and each current sensing element is multiplexed with a multiplexing device (MUX) into an analog-to-digital converter (ADC) which then transmits the data into a controlling and analyzing computer.

FIG. 14 shows a notional sequencing that the control and analysis computer of FIG. 13 would issue. It first selects a region to be acquired with a multiplexing device, then instructs the RF source to issue the drive signal, then acquires both the signal and drive, then analyzes the data.

FIG. 15 illustrates the conceptual layout of hardware along the length of a single programmable transmission line, similar to the passive line, but incorporating a programmable element for each region.

Figure 16:
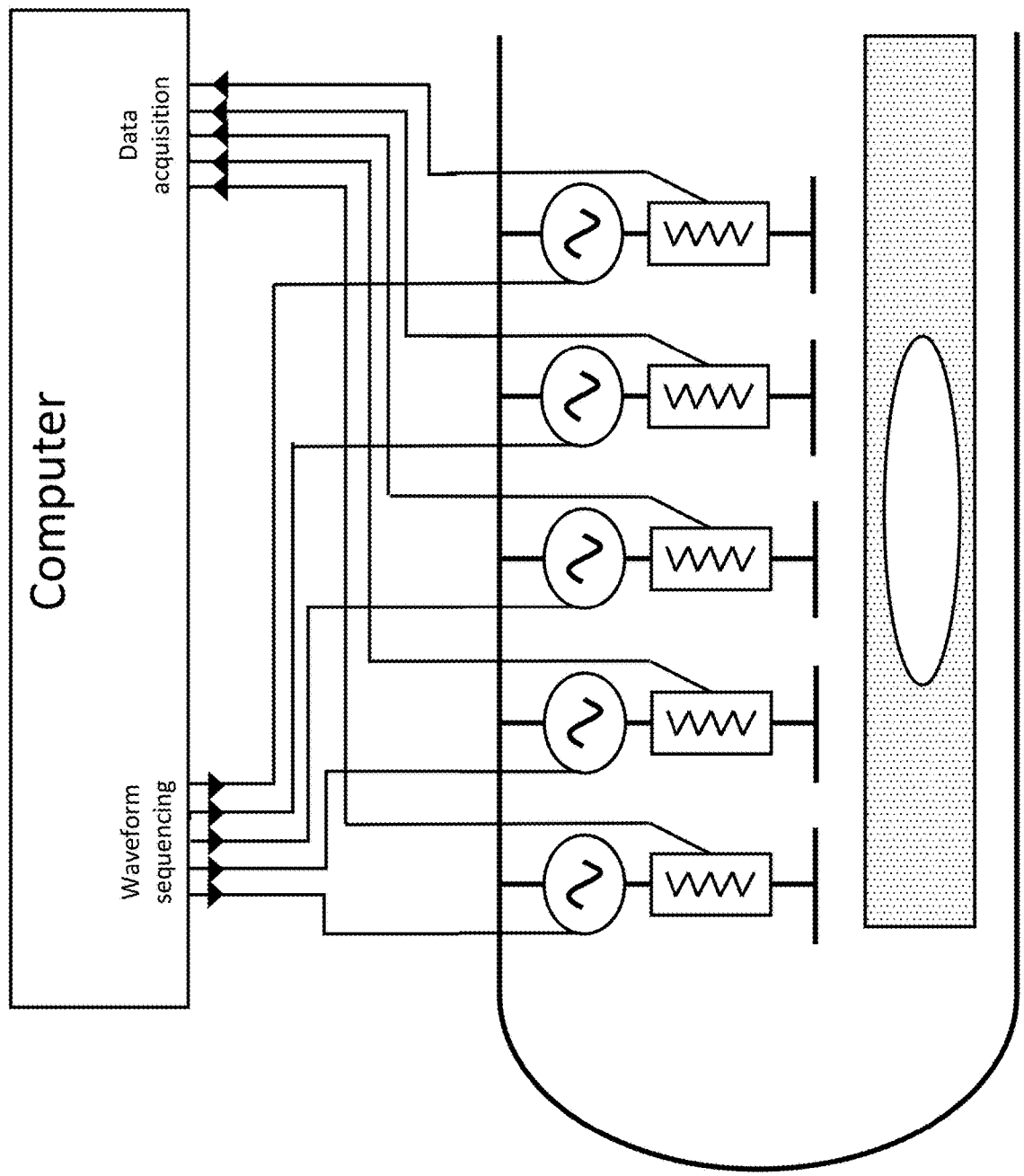
FIG. 16 illustrates the conceptual layout of hardware of a two-dimensional section for fully active sequencing of field propagation, according to various embodiments of the present technology.

FIG. 16 illustrates the conceptual layout of hardware of a two-dimensional section for fully active sequencing of field propagation.

Figure 17:
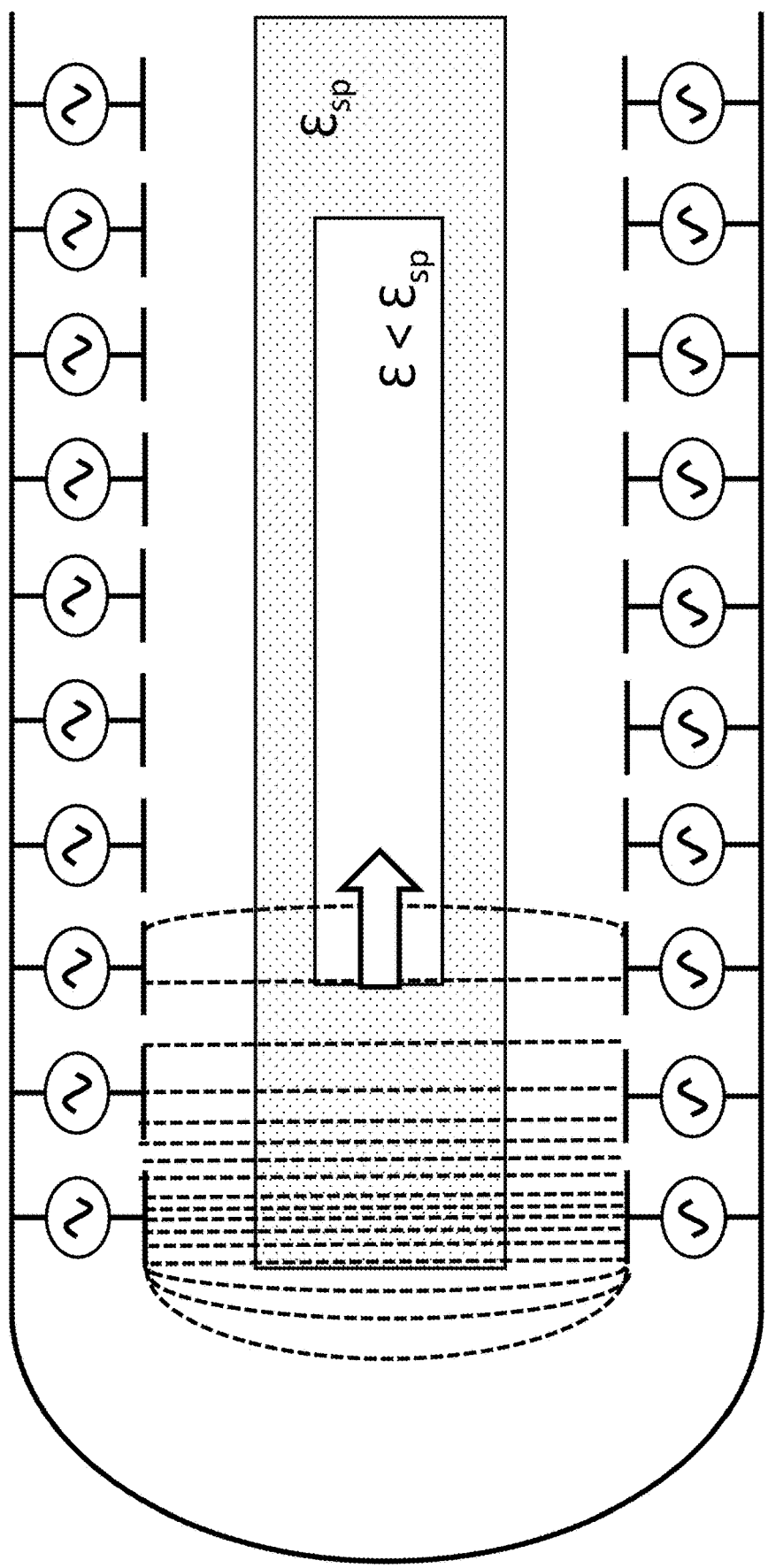
FIG. 17 illustrates the conceptual propagation of fields across a two-dimensional section of an active embodiment as the regional fields sources are sequenced from left to right, according to various embodiments of the present technology.

FIG. 17 illustrates the conceptual propagation of fields across a two-dimensional section of an active embodiment as the regional fields sources are sequenced from left to right.

FIG. 18 illustrates the conceptual propagation of fields in a two-dimensional section of an active embodiment as the regional fields sources are sequenced in outward or radial patterns.

FIG. 19 illustrates the concept of region tilting by adjusting the field producing elements in an active embodiment such that the regions are angled from the lower left to upper right as they propagate into the page in direction 1905.

Figure 20:
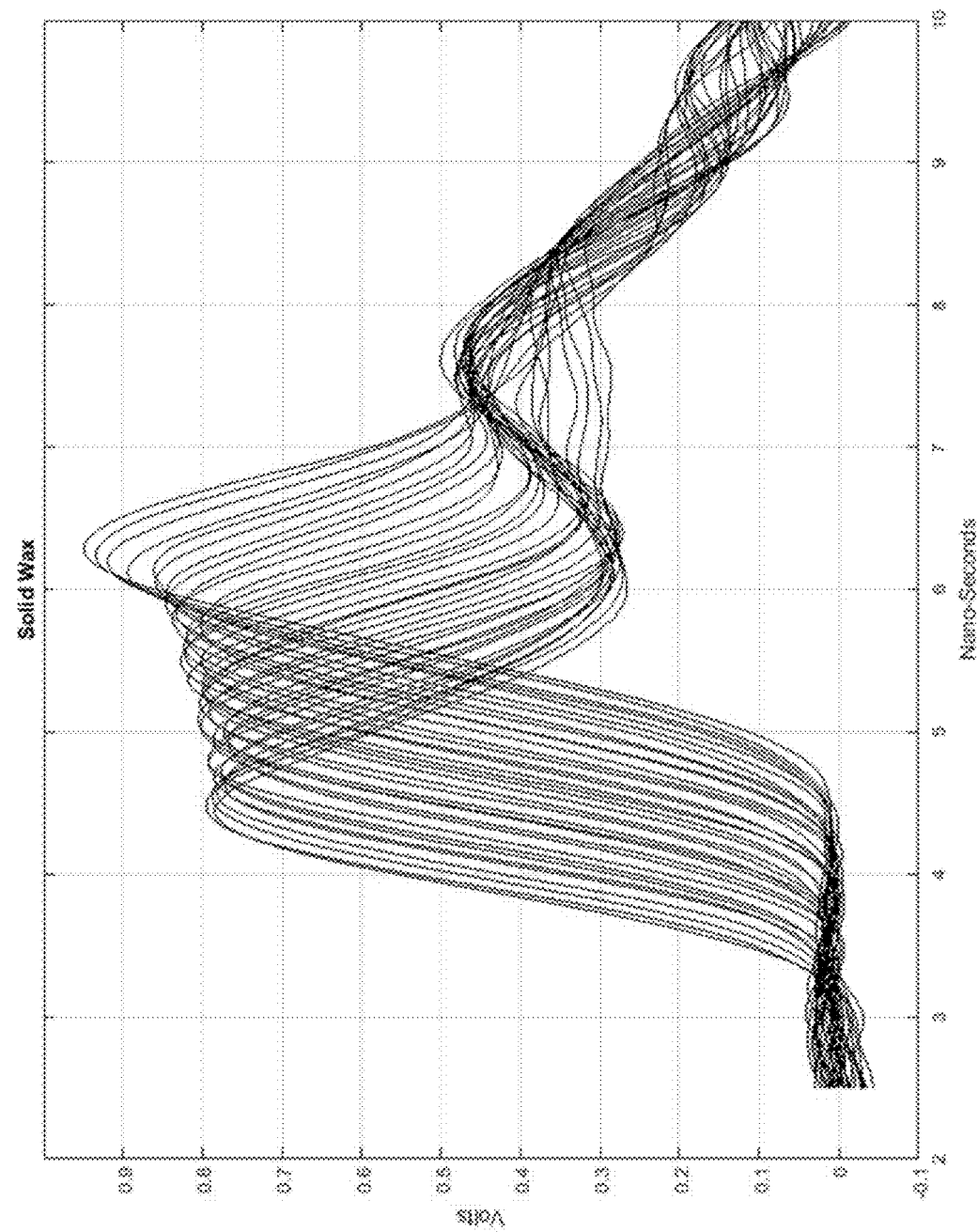
FIG. 20 illustrates a graph of voltage data from a specimen of solid wax gathered as a pulse moves from region to region along a transmission line-based system according to embodiments of the present technology.

FIG. 20 illustrates a graph 2000 of topographic data from a specimen of solid wax ($\varepsilon_r$=2.2) generated using a system according to embodiments of the present technology. In contrast to FIG. 21, no valley or peak is shown as pulse voltage is measured in regions spanning the specimen of solid wax. The slight upward ramping of successive pulse heights is due to instrumentation error.

Figure 21:
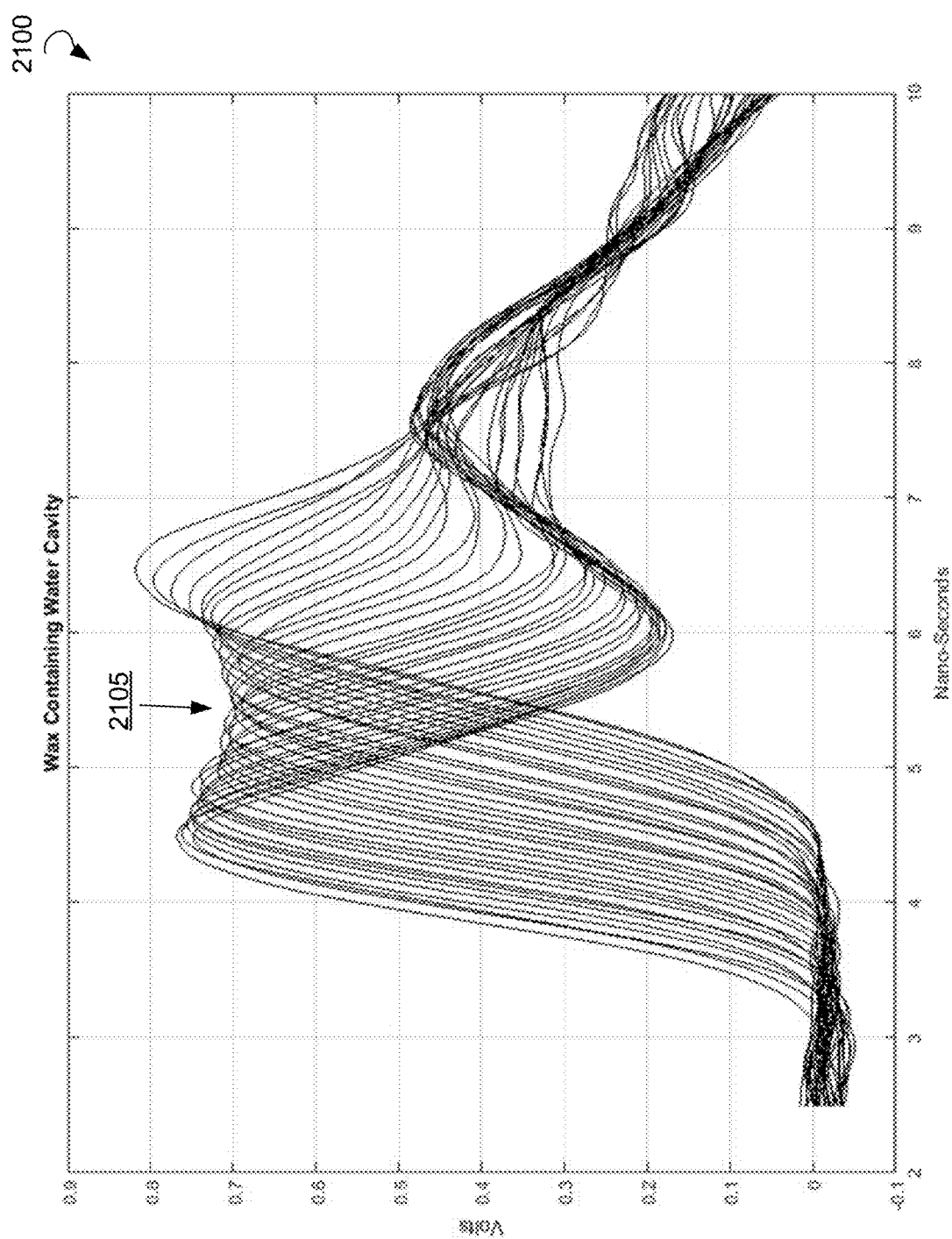
FIG. 21 illustrates a graph of voltage data from a specimen of solid wax containing a water cavity gathered as a pulse moves from region to region along a transmission-line based system according to embodiments of the present technology.

FIG. 21 illustrates a graph 2100 of topographic data from a specimen of wax containing an embedded water cavity ($\varepsilon_r$=80) generated using a system according to embodiments of the present technology. As described in FIG. 11, pulse current waveforms are measured at points along the length of a first conductor 1105 and second conductor 1110. FIG. 11 also shows pulse current waveforms 1103 that have a lower current illustrating the valley 1130 on the pulse current waveforms 1103 corresponding with the features of lesser dielectric constant 1120. Similarly, the pulse voltage waveforms of FIG. 21 show a valley 2105 indicating a water cavity of higher dielectric in the specimen for the same reasons of the valley 1130 of FIG. 11.

Figure 22:
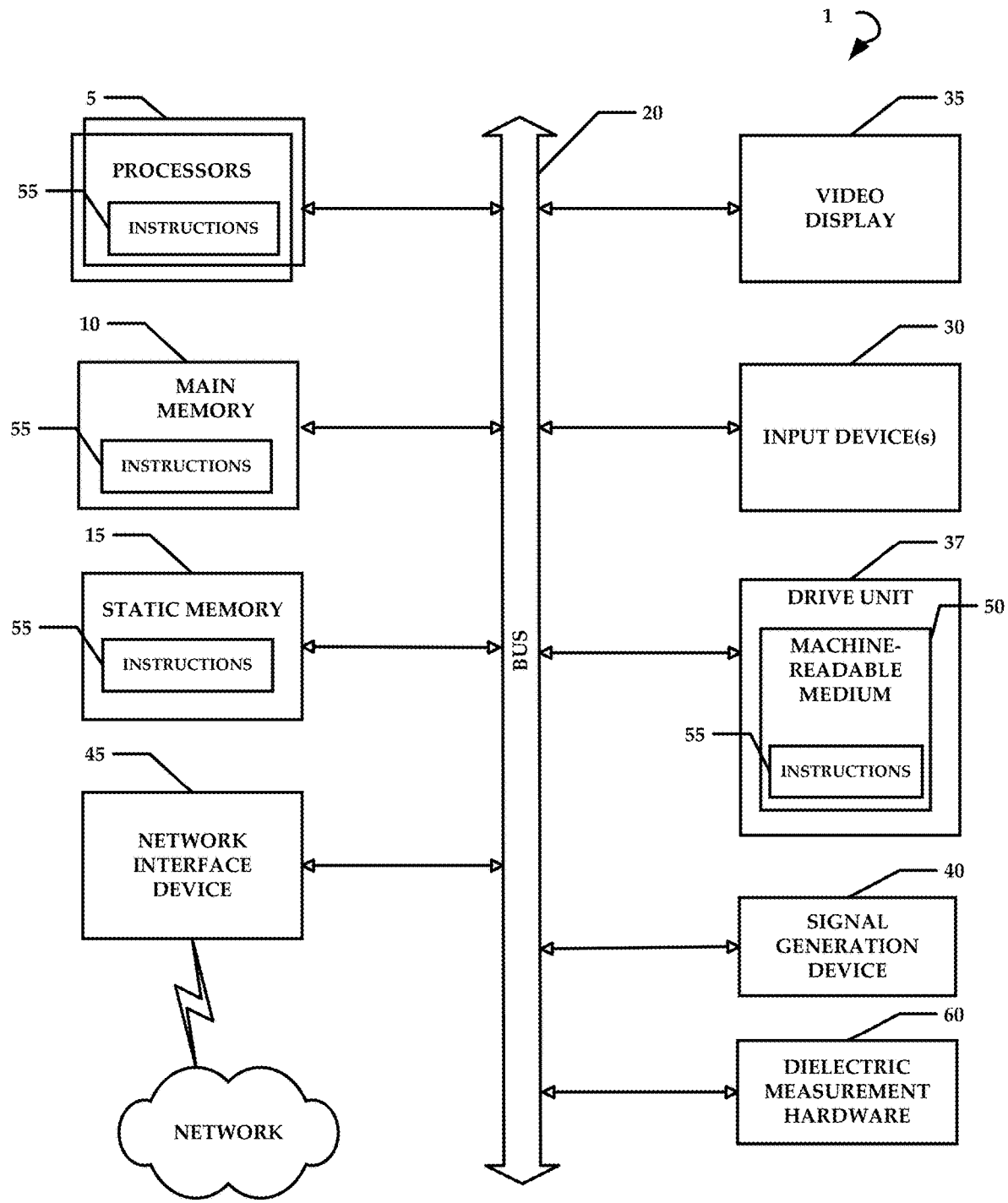
FIG. 22 illustrates a diagrammatic representation of an example machine in the form of a computing system within which a set of instructions for causing the machine to perform any one or more of the methodologies discussed herein is executed.

FIG. 22 is a diagrammatic representation of an example machine in the form of a computer system 1, within which a set of instructions for causing the machine to perform any one or more of the methodologies discussed herein may be executed. For example, programming a propagation velocity or pattern to iteratively refine data. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), an embedded computer, a field programmable gate array (FPGA), an application specific integrated circuit (ASIC), a tablet PC, a cellular telephone, a portable media device (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alpha-numeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), a network interface device 45, and dielectric measurement hardware 60. The computer system 1 may further include a data encryption module (not shown) to encrypt data.

The disk drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

These computer program instructions may also be stored in a computer readable medium that can direct a computer, other programmable data processing apparatus, or other devices to function in a particular manner, such that the instructions stored in the computer readable medium produce an image, tomograph, or analytic product derived from said image or tomograph, or constituent data thereof including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

In the description, for purposes of explanation and not limitation, specific details are set forth, such as particular embodiments, procedures, techniques, etc. in order to provide a thorough understanding of the present technology. However, it will be apparent to one skilled in the art that the present technology may be practiced in other embodiments that depart from these specific details.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel, or may be performed at different times.

While various embodiments have been described above, it should be understood that they have been presented by way of example only, and not limitation. The descriptions are not intended to limit the scope of the present technology to the particular forms set forth herein. To the contrary, the present descriptions are intended to cover such alternatives, modifications, and equivalents as may be included within the spirit and scope of the present technology as appreciated by one of ordinary skill in the art. Thus, the breadth and scope of a preferred embodiment should not be limited by any of the above-described exemplary embodiments.

What is claimed is:

1. A system for determining characteristics of a specific region within an inhomogeneous dielectric specimen by guiding propagation of electric fields through the inhomogeneous dielectric specimen, the system comprising:

at least one source of electromagnetic energy for generating electromagnetic waveforms, the electromagnetic waveforms comprising electric fields propagating along a prescribed path that defines a series of spatial regions through which the electric fields propagate, the prescribed path comprising electric field modulating elements that determine a rate of electric field propagation along the prescribed path;

a plurality of conductors for guiding the electric field propagation through an inhomogeneous dielectric specimen in the prescribed path, the electric fields spanning between two or more of the plurality of conductors as the electric fields propagate along the prescribed path, the plurality of conductors being external to the inhomogeneous dielectric specimen;

a plurality of measurement points for determining a measurement of the electric fields propagating along the prescribed path, the measurement of the electric fields used to determine regional dielectric characteristics of the inhomogeneous dielectric specimen and dielectric characteristics of the specific region within the inhomogeneous dielectric specimen;

at least one processor; and a memory storing processor-executable instructions, wherein the at least one processor is configured to implement the following operations upon executing the processor-executable instructions:

determining an effective dielectric constant of the specific region within the inhomogeneous dielectric specimen;

determining whether the effective dielectric constant of the specific region within the inhomogeneous dielectric specimen is consistent with the rate of the electric field propagation along the prescribed path;

modulating the electric field propagation along the prescribed path when the effective dielectric constant of the specific region within the inhomogeneous dielectric specimen is not consistent with the rate of the electric field propagation along the prescribed path;

measuring waveforms using the electric field propagation through the specific region within the inhomogeneous dielectric specimen; and determining features of the specific region within the inhomogeneous dielectric specimen using the waveforms.

2. The system of claim 1, wherein the plurality of conductors for guiding the electric field propagation through the inhomogeneous dielectric specimen in the prescribed path comprise a first conductor parallel to a second conductor.

3. The system of claim 1, wherein the plurality of conductors for guiding the electric field propagation through the inhomogeneous dielectric specimen in the prescribed path comprise an array of parallel conductor pairs.

4. The system of claim 3, wherein each pair of the array of parallel conductor pairs are opposed on opposite sides of the inhomogeneous dielectric specimen.

5. The system of claim 3, wherein each pair of the array of parallel conductor pairs are adjacent to each other on a same side of the inhomogeneous dielectric specimen.

6. The system of claim 1, wherein the electromagnetic waveforms along the prescribed path are sequenced across the plurality of conductors, the sequenced electromagnetic waveforms being used to create a dynamic prescribed propagation path and a dynamic rate of electric field propagation.

7. The system of claim 1, wherein the plurality of conductors for guiding the electric field propagation through the inhomogeneous dielectric specimen in the prescribed path comprise an array of discrete conductors.

8. The system of claim 7, wherein the electromagnetic waveforms along the prescribed path are sequenced across pairs of the array of discrete conductors, the sequenced electromagnetic waveforms used to create a dynamic prescribed propagation path and a dynamic rate of electric field propagation.

9. The system of claim 1, wherein the electric field modulating elements that determine the rate of electric field propagation along the prescribed path comprise physical delay structures, the physical delay structures slowing the rate of electric field propagation along the prescribed path and decreasing a speed of electromagnetic waves along the prescribed path.

10. The system of claim 1, wherein the electric field modulating elements that determine the rate of electric field propagation along the prescribed path comprise electronic components, the electronic components controlling the rate of electric field propagation along the prescribed path and controlling a speed of electromagnetic waves along the prescribed path.

11. The system of claim 1, wherein the electric field modulating elements that determine the rate of electric field propagation along the prescribed path comprise active electronic components, the active electronic components generating electric fields to screen against parasitic effects.

12. The system of claim 1, wherein the measurement of the electric fields propagating along the prescribed path measures one or more of: voltage, current, phase, and strength of the electric fields propagating along the prescribed path.

13. The system of claim 1, wherein the at least one processor is further configured to implement the following operations upon executing the processor-executable instructions:

generating a tomograph of the inhomogeneous dielectric specimen using the features of the specific region within the inhomogeneous dielectric specimen.

14. The system of claim 1, further comprising auxiliary sensors, the auxiliary sensors measuring an air gap between the plurality of conductors and the inhomogeneous dielectric specimen in the prescribed path.

15. The system of claim 14, wherein the at least one processor is further configured to implement the following operations upon executing the processor-executable instructions:

measuring the air gap between the plurality of conductors and the inhomogeneous dielectric specimen in the prescribed path; and adjusting the determining the effective dielectric constant of the specific region within the inhomogeneous dielectric specimen using the measuring of the air gap to increase accuracy of the determining the effective dielectric constant.

16. A system for determining characteristics of a specific region within an inhomogeneous dielectric specimen by guiding propagation of electric fields through the inhomogeneous dielectric specimen, the system comprising:

at least one source of electromagnetic energy for generating electromagnetic waveforms, the electromagnetic waveforms comprising electric fields propagating along a prescribed path that defines a series of spatial regions through which the electric fields propagate, the prescribed path comprising electric field modulating elements that determine a rate of electric field propagation along the prescribed path;

a plurality of conductors for guiding the electric field propagation through an inhomogeneous dielectric specimen in the prescribed path, the electric fields spanning between two or more of the plurality of conductors as the electric fields propagate along the prescribed path, the plurality of conductors being external to the inhomogeneous dielectric specimen;

a plurality of measurement points for determining a measurement of the electric fields propagating along the prescribed path, the measurement of the electric fields used to determine regional dielectric characteristics of the inhomogeneous dielectric specimen and dielectric characteristics of the specific region within the inhomogeneous dielectric specimen;

at least one processor; and a memory storing processor-executable instructions, wherein the at least one processor is configured to implement the following operations upon executing the processor-executable instructions:

determining an effective dielectric constant of the specific region within the inhomogeneous dielectric specimen;

determining whether the effective dielectric constant of the specific region within the inhomogeneous dielectric specimen is consistent with the rate of the electric field propagation along the prescribed path;

modulating the electric field propagation along the prescribed path when the effective dielectric constant of the specific region within the inhomogeneous dielectric specimen is not consistent with the rate of the electric field propagation along the prescribed path;

generating waveforms using the electric field propagation through the specific region within the inhomogeneous dielectric specimen; and determining features of the specific region within the inhomogeneous dielectric specimen using the waveforms.

17. The system of claim 16, wherein the electric field modulating elements that determine the rate of electric field propagation along the prescribed path comprise physical delay structures, the physical delay structures slowing the rate of electric field propagation along the prescribed path and decreasing a speed of electromagnetic waves along the prescribed path.

18. The system of claim 16, wherein the electric field modulating elements that determine the rate of electric field propagation along the prescribed path comprise electronic components, the electronic components controlling the rate of electric field propagation along the prescribed path and controlling a speed of electromagnetic waves along the prescribed path.

19. A system for determining characteristics of a specific region within an inhomogeneous dielectric specimen by guiding propagation of electric fields through the inhomogeneous dielectric specimen, the system comprising:

at least one source of electromagnetic energy for generating electromagnetic waveforms, the electromagnetic waveforms comprising electric fields propagating along a prescribed path that defines a series of spatial regions through which the electric fields propagate, the prescribed path comprising electric field modulating elements that determine a rate of electric field propagation along the prescribed path;

a plurality of conductors for guiding the electric field propagation through an inhomogeneous dielectric specimen in the prescribed path, the electric fields spanning between two or more of the plurality of conductors as the electric fields propagate along the prescribed path, the plurality of conductors being external to the inhomogeneous dielectric specimen;

auxiliary sensors, the auxiliary sensors measuring an air gap between the plurality of conductors and the inhomogeneous dielectric specimen in the prescribed path; and a plurality of measurement points for determining a measurement of the electric fields propagating along the prescribed path, the measurement of the electric fields used to determine regional dielectric characteristics of the inhomogeneous dielectric specimen and dielectric characteristics of the specific region within the inhomogeneous dielectric specimen.

* * * * *